US006831088B2

(12) United States Patent
Fish et al.

(10) Patent No.: US 6,831,088 B2
(45) Date of Patent: Dec. 14, 2004

(54) 3-HETEROCYCLYPROPANOHYDROXAMIC ACID PCP INHIBITORS

(75) Inventors: Paul Vincent Fish, Sandwich (GB); Jackie Diane Kendall, Sandwich (GB); Gavin Alistair Whitlock, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/643,476

(22) Filed: Aug. 19, 2003

(65) Prior Publication Data

US 2004/0058917 A1 Mar. 25, 2004

Related U.S. Application Data

(62) Division of application No. 10/109,756, filed on Mar. 29, 2002, now Pat. No. 6,645,993.
(60) Provisional application No. 60/293,419, filed on May 24, 2001.

(30) Foreign Application Priority Data

Mar. 30, 2001 (GB) .............................................. 0108097

(51) Int. Cl.[7] ...................... A61K 31/422; A61K 31/44; C07D 263/30; C07D 413/12
(52) U.S. Cl. ...................... 514/312; 514/340; 514/374; 546/153; 546/271.4; 548/236
(58) Field of Search ......................... 548/236; 546/153, 546/271.4; 514/312, 340, 374

(56) References Cited

U.S. PATENT DOCUMENTS

| | | | | |
|---|---|---|---|---|
| 5,304,604 A | * | 4/1994 | Davidson et al. | ......... 514/238.2 |
| 5,861,380 A | * | 1/1999 | Gyorkos et al. | .............. 514/19 |
| 6,448,278 B2 | * | 9/2002 | Bailey et al. | ................ 514/364 |
| 6,645,993 B2 | * | 11/2003 | Fish et al. | ................... 514/374 |
| 6,716,861 B2 | * | 4/2004 | Datta et al. | .................. 514/364 |

FOREIGN PATENT DOCUMENTS

| | | |
|---|---|---|
| WO | WO 95/23790 | 9/1995 |
| WO | WO 97/05865 | 2/1997 |
| WO | WO 99/45927 | 9/1999 |
| WO | WO 00/37436 | 6/2000 |
| WO | WO 00/51993 | 9/2000 |
| WO | WO 01/47901 | 7/2001 |

OTHER PUBLICATIONS

Dankwardt, et al, "Solid–Phase Synthesis of Di– and Tripeptid Hydroxamic Acids as Inhibitors of Procollagen C–Proteinase", Bioorganic & Medical Chemistry Letters 10 (2000); pp 2513–2516.
Fray, et al, "Selectivity of Inhibition of Matrix Metalloproteases MMP–3 and MMP–2 by Succinyl Hydroxamates and their Carboxylic Acid Analogues is Dependent on P3' Group Chirality", Bioorganig & Medicinal Chemistry Letters 11 (2000); pp 567–570.

Fessler, et al, "Biosynthesis of Procollagen", Ann. Rev. Biochem. 1978, vol. 47; pp. 129–162.
Goldberg, et al, "Procollagen Peptides: Its Mode of Action on the Native Substrate", Cell., 1975, vol. 4; pp 45–50.
Kessler, et al, "A Method for Assaying the Activity of the Endopeptidase Which Excises the Nonhelical Carboxyterminal Extension from Type I Procollagen", Analytical Biochemistry, 1978, vol. 86, pp. 461–169.
Duksin, et al, "The Role of Glycosylation in the Enzymatic Conversion of Procollagen to Collagen: Studies Using Tunicamycin and Concanavalin A", Archives of Biochemistry and Biophysics, 1978, vol. 185, No. 2; pp. 326–332.
Leung, et al, "Separate Amino and Carboxyl Procollagen Peptidases in Chick Embryo Tendon", The Journal of Biological Chemistry, 1979, vol. 254, No. 1, pp 224–232.
Davidson, et al, "Procollagen Processing", Eur. J. Biochem., vol. 100, 1979, pp 551–558.
Njieha, et al, "Partial Purification of a Procollagen C–Proteinase. Inhibition by Synthetic Peptides and Sequential Cleavage of Type I Procollagen", Biochemistry, 1982, vol. 21, pp. 757–764.
Hojima, et al, "Type I Procollagen Carboxyl–terminal Proteinase from Chick Embryo Tendous", The Journal of Biological Chemistry, 1985, vol. 260, No. 29, pp. 15996–16003.
Kessler, et al, "Type I procollagen c–proteinase from mouse fibroblasts", Eur. J. Biochem., 1989, vol. 180, pp. 115–121.
Kessler, et al, "Partial Purification and Characterization of a Procollagen C–Proteinase from rhe Culture Medium of Mouse Fibroblasts", Collagen Rel. Res., 1986, vol. 6; pp 249–266.
Fertala, et al, "Self–assembly intop Fibrils of Collagen II by Enzymic Cleavage of Recombinant Procollagen II", The Journal of Biological Chemistry, 1994, vol. 269, No. 15; pp 11584–11589.
Ryhanen, et al, "Conversion of Type II Procollagen to Collagen in Vitro: Removal of the Carboxyl–Terminal Extension Is Inhibited by Several Naturally Occurring Amino Acids., Polyamines and Structurally Related Compounds", Archives of Biochemistry and Biophysics, 1982, vol. 215, No. 1, pp.

(List continued on next page.)

Primary Examiner—Golam M M Shameem
(74) Attorney, Agent, or Firm—J. Michael Dixon

(57) ABSTRACT

Compounds of formula (1):

and their salts, solvates, prodrugs, etc., wherein the substituents have the values mentioned herein, are Procollagen C-Proteinase (PCP) inhibitors and have utility in conditions mediated by PCP.

17 Claims, No Drawings

OTHER PUBLICATIONS

Pilcher, et al, "The Activity of Collagenase–1 Is Required for Keratinocyte Migration on a Type I Collagen Matrix", The Journal of Cell Biology, 1997, vol. 137, No. 6, pp 1445–1457.

Agren, M.S., "Gelatinase activity during would healing", British Journal of Dermatology, 1994, vol. 131, pp 634–640.

Salo, et al, "Expression Matrix Metalloproteinase–2 and –9 during Early Human Wound Healing", Laboratory Investigation, 1994, vol.: 70, No. 2; pp 176–182.

Taraboletti, et al, "Inhibition of Angiogenesis and Murine Hemangioma Growth by Batimastat, a Synthetic Inhibitor of Matrix Metalloproteinases", Journal of the National Caner Institute. 1995. vol. 87, No. 4: pp 293–299.

Zask, et al, "Inhibition of Matrix Metalloproteinases: Structure Based Design", Current Pharmaceutical Design, 1996, vol. 2; pp 624–661.

Beckett, et al, "Recent advances in matrix metalloproteinase inhibitor research", DDT, 1996, vol. 1, No. 1; pp 16–26.

Prokop, et al, "Geritable Diseases of Collagen", The New England Journal of Medicine, vol. 344, No. 6, pp 376–383.

Kuhn, "The Classical Collagens: Types I, II, and III", Structure and Function of Collagen Types, 1987; pp 1–42.

Evans, et al, "A General Method for the Synthesis of Enantiomerically Pure Beta–Substituted, Beta–Amino Acids through alpha–Substituted Succinic acid Derivatives", J. Org. Chem., 1999, vol. 64; pp 6411–6417.

Simoneau, et al, "Discovery of Non–peptidic P2–P3 Butanediamide Renin Inhibitors with High Oral Efficacy", Bioorganic & Medicinal Chemistry, 1999, vol. 7, pp 489–508.

Yamamoto, et al, "Inhibition of Membrane–Type I Matrix Metalloproteinase by Hy droxamate Inhibitors: An Examination of the Subsite Pocket", J. Med. Chem., 1998, vol. 41; pp 1209–1217.

Steinman, et al, "The Design Synthesis, and Structure–Activity Relationships of a Series of Macrocyclic MMP Inhibitors", Bioorganic & Medicinal Chemistry Letters 8, 1998, pp 2087–2092.

Vu, et al, "Nonpeptidic SH2 Inhibitors of the Tyrosine Kinase Zap–70", Bioorganic & Medicinal Chemistry Letters 9, 1999, pp 3009–3014.

Fray, et al, "Application of Epimerisation–Free amide Coupling Conditions to the Synthesis of Matrix Metalloprotease Inhibitor Intermediates", Tetrahedron 54, 1998; pp 13825–13832.

Floyd, et al, "Rapid Synthesis of Matrix Metalloproteinase Inhibitors via Ugi Four–Compnent Condensation", Synlett, 1998; pp 637–639.

McClure, et al, 1998, vol. 8, No. 2, pp 143.

Chem. Abs., 1997:594709.

Bornstein, et al, "The Proteins", Academic Press, New York, 1979, pp 412–632.

Kivirikko, et al, "Extracellur Matrix Biochemistry", Elsevier Science Publishing Co., Inc., New York, pp 83–118.

Kuhn, et al, "Structure and Function of Collagen Types", Academic Press, Inc., 1987, pp 1–42.

* cited by examiner

3-HETEROCYCLYPROPANOHYDROXAMIC ACID PCP INHIBITORS

This application is a divisional of U.S. patent application Ser. No. 10/109,756 filed Mar. 29, 2002, now U.S. Pat. No. 6,645,993, which claims the benefits of U.S. provisional application No. 60/293,419 filed May 24, 2001.

This invention relates to a certain class of compounds, and the pharmaceutically acceptable salts, solvates and prodrugs thereof, which Inhibit Procollagen C-proteinase ("PCP"). They are therefore useful in the treatment of mammals having conditions alleviable by inhibition of PCP. Especially of interest is an antiscarring treatment for wounds.

Fibrotic tissues, including dermal scars, are characterised by excessive accumulation of extracellular matrix, mainly collagen type 1. It is thought that inhibition of collagen deposition will reduce formation of scar tissue. Collagen is secreted as the precursor, procollagen, which is transformed into the insoluble collagen by cleavage of the C-terminal propeptide by PCP. PCP is a zinc-dependent metalloprotease which is secreted from TGF-β-activated fibroblasts belonging to the subfamily of astacin-like proteases and able to cleave the C-terminal peptide of types I, II and III procollagens. Furthermore, data suggest that PCP activates lysyl oxidase, an enzyme essential for the formation of covalent cross-links which stabilise the fibrous form of collagen. Therefore, inhibition of PCP may not only reduce collagen deposition but may also make collagen more accessible for degradation.

Collagen is integral to, among other things, the proper formation of connective tissue. Thus, the over- or under-production of collagen or the production of abnormal collagen (including incorrectly processed collagen) has been linked with numerous connective tissue diseases and disorders. Mounting evidence suggests that PCP Is an essential key enzyme for the proper maturation of collagen (see for example International Patent Application publication number WO 97/05865).

The present invention relates to substances capable of inhibiting PCP activity in order to regulate, modulate and/or reduce collagen formation and deposition. More specifically, the invention relates to the use of compounds and pharmaceutical compositions thereof for the treatment of various conditions relating to production of collagen.

At present more than nineteen types of collagens have been identified. These collagens, including fibrillar collagen types I, II, III are synthesized as procollagen precursor molecules which contain amino- and carboxy-terminal peptide extensions. These peptide extensions, referred to as "pro-regions," are designated as N- and C-propeptides, respectively. The pro-regions are typically cleaved upon secretion of the procollagen triple helical precursor molecule from the cell to yield a mature triple helical collagen molecule. Upon cleavage, the "mature" collagen molecule is capable of association, for example, into highly structured collagen fibers. See e.g., Fessler and Fessler, 1978, Annu. Rev. Biochem. 47:129–162; Bornstein and Traub, 1979, in: The Proteins (eds. Neurath, H. and Hill, R. H.), Academic Press, New York, pp. 412–632; Kivirikko et al., 1984, in: Extracellur Matrix Biochemistry (eds. Piez, K. A. and Reddi. A. H.), Elsevier Science Publishing Co., Inc., New York, pp. 83–118; Prockop and Kivirikko, 1984, N. Engl, J. Med. 311:376–383; Kuhn, 1987, in: Structure and Function of Collagen Types (eds. Mayne, R. and Burgeson, R. E.), Academic Press, Inc., Orlando, Fla., pp. 1–42.

An array of conditions has been associated with the inappropriate or unregulated production of collagen, including pathological fibrosis or scarring, including endocardial sclerosis, idiopathic interstitial fibrosis, interstitial pulmonary fibrosis, perimuscular fibrosis, Symmers' fibrosis, pericentral fibrosis, hepatitis, dermatofibroma, cirrhosis such as billary cirrhosis and alcoholic cirrhosis, acute pulmonary fibrosis, idiopathic pulmonary fibrosis, acute respiratory distress syndrome, kidney fibrosis/glomerulonephritis, kidney fibrosis/diabetic nephropathy, scieroderma/systemic, scleroderma/local, keloids, hypertrophic scars, severe joint adhesions/arthritis, myelofibrosis, comeal scarring, cystic fibrosis, muscular dystrophy (duchenne's), cardiac fibrosis, muscular fibrosis/retinal separation, esophageal stricture and Pyronie's disease. Further fibrotic disorders may be induced or Initiated by surgery, including scar revision/plastic surgeries, glaucoma, cataract fibrosis, corneal scarring, joint adhesions, graft vs. host disease, tendon surgery, nerve entrapment, dupuytren's contracture, OB/GYN adhesions/fibrosis, pelvic adhesions, peridural fibrosis, restenosis. Other conditions where collagen plays a key role include burns. Fibrosis of lung tissue is also observed in patients suffering from chronic obstructive airways disease (COAD) and asthma. One strategy for the treatment of these diseases and conditions is to inhibit the overproduction and/or deposition and/or unregulation of collagen. Thus, identification and isolation of molecules which control, inhibit and/or modulate the production and deposition of collagen are of major medical interest.

Recent evidence suggests that PCP is the essential key enzyme that catalyzes the cleavage of the Procollagen C-propeptide. This has been demonstrated in fibrillar collagens, including type I, type I, and type III collagen.

PCP was first observed in the culture media of human and mouse fibroblasts (Goldberg et al., 1975, Cell 4:45–50; Kessler and Goldberg, 1978, Anal. Biochem. 86:463–469), and chick tendon fibroblasts (Duskin et al., 1978, Arch. Biochem. Biophys. 185:326–332; Leung et al., 1979, J. Biol, Chem. 254:224–232). An acidic proteinase which removes the C-terminal propeptides from type I procollagen has also been identified (Davidson et al., 1979, Eur. J. Biochem. 100:551).

A partially purified protein having PCP activity was obtained from chick calvaria in 1982. Njieha et al., 1982, Biochemistry 23:757–764. In 1985, chicken PCP was Isolated, purified and characterized from conditioned media of chick embryo tendons. Hojima et al., 1985, J. Biol. Chem. 260:15996–16003. Murine PCP has been subsequently purified from media of cultured mouse fibroblasts. Kessler et al., 1986, Collagen Relat. Res. 6:249–266; Kessler and Adar, 1989, Eur. J. Biochem. 186:115–121. Finally, the cDNA encoding human PCP has been identified, as set forth in the above-referenced articles and references disclosed therein.

Experiments conducted with these purified forms of chick and mouse PCP have indicated that the enzyme is instrumental in the formation of functional collagen fibers. Fertala et al., 1994, J. Biol. Chem. 269:11584.

As a consequence of the enzyme's apparent importance to collagen production, scientists have identified a number of PCP Inhibitors. See e.g., Hojima et al., supra. For example, several metal chelators have demonstrated activity as PCP inhibitors. Likewise, chymostatin and pepstatin A were found to be relatively strong inhibitors of PCP. Additionally, $\alpha_2$-Macroglobuline, ovostatin, and fetal bovine serum appear to at least partially inhibit PCP activity.

Dithiothreitol, SDS, concanavalin A, $Zn^{2+}$, $Cu^{2+}$, and Cd2' are similarly reported to be Inhibitory at low concentrations. Likewise, some reducing agents, several amino acids, phosphate, and ammonium sulfate were inhibitory at concentrations of 1–10 mM. Further, the enzyme was shown to be inhibited by the basic amino acids lysine and arginine (Leung et al., supra; Ryhänen at al., 1982, Arch. Biochem. Biophys. 215:230–235). Finally, high concentrations of NaCl or Tris-HCl buffer were found to inhibit PCP's activity. For example, it is reported that, with 0.2, 0.3, and 0.5M NaCl, the activity of PCP was reduced 66, 38, and 25%, respectively, of that observed with the standard assay concentration of 0.15M. Tris-HCl buffer in a concentration of 0.2–0.5M markedly inhibited activity (Hojima et al., supra). PCP activity and its inhibition have been determined using a wide array of assays. See e.g., Kessler and Goldberg, 1978, Anal. Biochem. 86:463; Njieha et al., 1982, Biochemistry 21:757–764. As articulated in numerous publications, the enzyme is difficult to isolate by conventional biochemical means and the identity of the DNA sequence encoding such enzyme was not known until reported in the above referenced and related patent applications.

In view of its essential role in the formation and maturation of collagen PCP appears to be an ideal target for the treatment of disorders associated with the inappropriate or unregulated production and maturation of collagen. However, none of the inhibitors so far disclosed has proven to be an effective therapeutic for the treatment of collagen-related diseases and conditions.

The identification of effective compounds which specifically inhibit the activity of PCP to regulate and modulate abnormal or inappropriate collagen production is therefore desirable and the object of this invention. Matrix metalloproteases (MMPs) constitute a family of structurally similar zinc-containing metalloproteases, which are involved in the remodelling, repair and degradation of extracellular matrix proteins, both as part of normal physiological processes and in pathological conditions.

Another important function of certain MMPs is to activate other enzymes, including other MMPS, by cleaving the pro-domain from their protease domain. Thus, certain MMPs act to regulate the activities of other MMPs, so that over-production in one MMP may lead to excessive proteolysis of extracellular matrix by another, e.g. MMP-14 activates pro-MMP-2

During the healing of normal and chronic wounds, MMP-1 is expressed by migrating keratinocytes at the wound edges (U. K. Saarialho-Kere, S. O. Kovacs, A. P. Pentland, J. Clin. Invest. 1993, 92, 2858–66). There is evidence which suggests MMP-1 is required for keratinocyte migration on a collagen type I matrix in vitro, and is completely inhibited by the presence of the non-selective MMP Inhibitor SC44463 ((N-4-hydroxy)-N1-[(1S)-2-(4-methoxyphenyl)methyl-1-((1R)-methylamino)carbonyl)]-(2R)-2-(2-methylpropyl)butanediamide) (B. K. Pilcher, JA. Dumin, B. D. Sudbeck, S. M. Krane, H. G. Welgus, W. C. Parks, J. Cell Biol., 1997, 137, 1–13). Keratinocyte migration in vivo is essential for effective wound healing to occur.

MMP-2 and MMP-9 appear to play important roles in wound healing during the extended remodelling phase and the onset of re-epithelialisation, respectively (M. S. Agren, Brit. J. Dermatology, 1994, 131, 634–40; T. Salo, M. Mäkänen, M. Kylmäniemi, Lab. Invest., 1994, 70, 176–82). The potent, non-selective MMP inhibitor BB94 ((2S,3R)-5---methyl-3-{[(1S)1-1-(methylcarbamoyl)-2-phenylethyl]carbamoyl}-2-[(2-thienylthio)methyl]hexanohydroxamic acid, batimastat), inhibits endothelial cell invasion of basement membrane, thereby inhibiting angiogenesis (G. Tarboletti, A. Garofalo, D. Belotti, T. Drudis, P. Borsotti, E. Scanziani, P. D.

Brown, R. Glavazzi, J. Natl. Cancer Inst., 1995, 87, 293–8). There is evidence that this process requires active MMP-2 and/or 9.

Thus PCP inhibitors which significantly inhibit MMPs 1 and/or 2 and/or 9 would be expected to impair wound healing. MMP-14 is responsible for the activation of MMP-2, and thus inhibition of MMP-14 might also result in impaired wound healing.

For recent reviews of MMPs, see Zask et al, Current Pharmaceutical Design, 1996, 2, 624–661; Beckett, Exp. Opin. Ther. Patents, 1996, 6, 1305–1315; and Beckett et al, Drug Discovery Today, vol 1(no. 1), 1996, 16–26.

Alternative names for various MMPs and substrates acted on by these are shown in the table below (Zask et al, supra).

| Enzyme | Other names | Preferred substrates |
| --- | --- | --- |
| MMP-1 | Collagenase-1, interstitial collagenase | Collagens I, II, III, VII, X, gelatins |
| MMP-2 | Gelatinase A, 72 kDa gelatinase | Gelatins, collagens IV, V, VII, X, elastin, fibronectin; activates pro-MMP-13 |
| MMP-3 | Stromelysin-1 | Proteoglycans, laminin, fibronectin, gelatins. |
| MMP-7 | Pump, Matrilysin | Proteoglycans, laminin, fibronectin, gelatins, collagen IV, elastin, activates pro-MMP-1 and -2. |
| MMP-8 | Collagenase-2, neutrophil collagenase | Collagens I, II, III |
| MMP-9 | Gelatinase B, 92 kDa gelatinase | Gelatins, collagens IV, V, elastin |
| MMP-12 | Macrophage metalloelastase | Elastin, collagen IV, fibronectin, activates pro-MMP-2 & 3. |
| MMP-13 | Collagenase-3 | Collagens I, II, III, gelatins |
| MMP-14 | MT-MMP-1 | Activates pro-MMP-2 & 13, gelatins |
| MMP-15 | MT-MMP-2 | unknown |
| MMP-16 | MT-MMP-3 | Activates pro-MMP-2 |
| MMP-17 | MT-MMP-4 | unknown |

International Patent Applications PCT/IB00/01855 (published as WO 01/47901) and PCT/IB01/02360 (filed on 7$^{th}$ December 2001), and foreign equivalents thereof, describe various 3-heterocyclylpropanohydroxamic acid PCP Inhibitors. The teachings of both of these are herein incorporated by reference in their entirety.

According to one aspect of the present invention, there are provided compounds of formula (I):

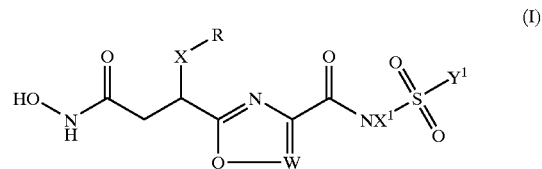

wherein:
X is $C_{1-6}$ alkylene, or $C_{2-4}$ alkenylene, each of which is optionally substituted by one or more fluorine atoms,
R is aryl, $C_{3-6}$ a cycloalkyl or $C_{5-8}$ cycloalkenyl optionally substituted by one or more fluorine atoms,
W is N or CZ,
Z is H, or $C_1$–$C_4$ alkyl optionally substituted with halogen,
$X^1$ is independently H or $C_1$–$C_4$ alkyl,
$Y^1$ is independently
$C_1$–$C_4$ alkyl, optionally substituted by aryl, or by one or more halogen atoms, with the proviso that when $Y^1$ is methyl, $X^1$ is not H,
or $Y^1$ is independently aryl, or a mono or bicyclic non-aromatic carbocyclic or heterocyclic moiety containing up to 10 ring atoms and which can include up to 3 ring heteroatoms, independently selected from N, O and S, which ring moiety is optionally substituted by one or more substituents independently selected from halogen, $C_1$–$C_4$ alkoxy or $C_1$–$C_4$ alkyl optionally substituted by one or more halogen,
and the pharmaceutically acceptable salts, solvates (including hydrates) and prodrugs thereof.

"Alkyl", "alkylene", "alkoxy", and "alkenylene" groups, Including groups incorporating said moieties, may be straight chain or branched where the number of carbon atoms allows.

'Aryl' is a mono or bicyclic aromatic carbocyclic or heterocyclic moiety containing up to 10 ring atoms, and which can include up to 3 ring heteroatoms, selected from N, O and S, which ring moiety is optionally substituted by one or more substituents, Independently selected from halogen, $C_1$–$C_4$ alkoxy, $C_1$–$C_4$ alkyl optionally substituted by one or more halogen.

Halogen is taken to mean fluorine, chlorine, bromine or iodine.

Pharmaceutically-acceptable salts are well known to those skilled in the art, and for example include those mentioned in the art cited above, and by Berge et al, in *J. Pharm. Sci.*, 66, 1–19 (1977). Suitable acid addition salts are formed from acids which form non-toxic salts and include the hydrochloride, hydrobromide, hydroiodide, nitrate, sulphate, bisulphate, phosphate, hydrogenphosphate, acetate, trifluoroacetate, gluconate, lactate, salicylate, citrate, tartrate, ascorbate, succinate, maleate, fumarate, gluconate, formate, benzoate, methanesulphonate, ethanesulphonate, benzenesulphonate, pamoate, camsylate, and p-toluenesulphonate salts.

Pharmaceutically acceptable base addition salts are well known to those skilled in the art, and for example include those mentioned in the art cited above, and can be formed from bases which form non-toxic salts and include the aluminium, calcium, lithium, magnesium, potassium, sodium and zinc salts, and salts of non-toxic amines such as diethanolamine.

Certain of the compounds of formula (I) may exist in one or more zwitterionic forms. It is to be understood that pharmaceutically acceptable salts includes all such zwitterions.

Certain of the compounds of formula (I), their salts, solvates, prodrugs, etc. may exist in one or more polymorphic forms. It is to be understood that the invention includes all such polymorphs.

The compounds of formula (I), their salts, hydrates, prodrugs etc. can exhibit isotopic variation, e.g. forms with enriched $^2H$, 3H, $^{13}C$, $^{14}C$, $^{15}N$, $^{18}O$, etc. may be prepared, for example by suitable variation of the synthetic methods described herein using methods and reagents known in the art or routine modification thereof. All such isotopic variants are included in the scope of the invention.

Prodrug moieties are well-known to those skilled in the art (see for example the article by H Feres, in Drugs of Today, vol 19, no.9 (1983) pp.499–538, especially section A1), and for example include those specifically mentioned in A. A. Sinkula's article in Annual Reports in Medicinal Chemistry, vol 10, chapter 31, pp.306–326, herein incorporated by reference, and the references therein. Specific prodrug moieties which may be specifically mentioned are aliphatic-aromatic, carbonate, phosphate and carboxylic esters, carbamates, peptides, glycoside, acetals and ketals, tetrahydropyranyl and silyl ethers. Such prodrug moieties can be cleaved in situ, e.g. are hydrolysable in physiological conditions, to give compounds of formula (1).

Certain of the compounds of the formula (I) may exist as geometric isomers. Certain of the compounds of the formula (I) may exist in one or more tautomeric forms. The compounds of the formula (I) may possess one or more asymmetric centres, apart from the specified centres in formula (1), and so exist in two or more stereoisomeric forms. The present invention includes all the individual stereoisomers, tautomers and geometric isomers of the compounds of formula (I) and mixtures thereof.

Preferably the compounds of formula (1) have the following stereochemistry (IA):

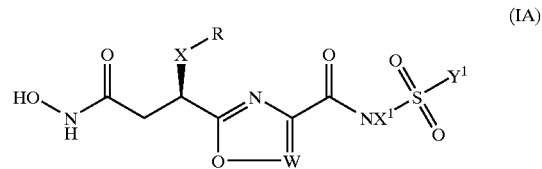

(IA)

Preferably X is a linear $C_{2-4}$ alkylene moiety optionally substituted by one or more fluorine atoms.
Most preferably X is propylene.
Preferably R is $C_{3-4}$ cycloalkyl optionally substituted by one or more fluorine atoms. More preferably R is cyclobutyl or cyclohexyl optionally substituted by one or more fluorine atoms.
Yet more preferably R is cyclobutyl or cyclohexyl.
Most preferably R is cyclohexyl.
Preferably W Is N, CH or CCH$_3$.
Most preferably W is N.
Preferably $Y^1$ is $C_1$–$C_4$ alkyl optionally substituted by phenyl or by one or more halogen atoms, or $Y^1$ is phenyl, optionally substituted by one or more substituents independently selected from halogen, $C_1$–$C_4$ alkoxy, $C_1$–$C_4$ alkyl optionally substituted with one or more halogen, and which phenyl ring is optionally pyrido-fused, or $Y^1$ is a 5- or 6-membered heterocyclic ring, which can include one or two heteroatoms selected from N, O and S, which heterocyclic ring optionally substituted by one or more substituents independently selected from halogen, $C_1$–$C_4$ alkoxy, $C_1$–$C_4$ alkyl optionally substituted with one or more halogen.
More preferably $Y^1$ is phenyl, 4-methylphenyl, 4-methoxyphenyl, 4-fluorophenyl, 4-isopropylphenyl, 3,4-dimethoxyphenyl, 8-quinolinyl, 3,5-dimethyl-4-isoxazolyl, isopropyl, methyl, benzyl or 3-pyridyl.
Even more preferably $Y^1$ is phenyl, benzyl, 3,4-dimethoxyphenyl, or pyridyl.
Most preferably $Y^1$ is phenyl.
Preferably $X^1$ is H or methyl.
Most preferably $X^1$ is H.
A preferred group of compounds is that in which each substituent is as specified in the Examples below.
Another preferred group of compounds are those of the examples below and the salts, solvates and prodrugs thereof.
Another aspect of the invention is a compound of formula (I) described herein, and the salts, solvates and prodrugs thereof, for use in medicine.
Another aspect of the invention is a compound of formula (I) described herein, and the salts, solvates and prodrugs thereof, for use as medicament for the treatment of a PCP-mediated condition or disease.
Another aspect of the invention is the use of a compound of formula (1) described herein, and the salts, solvates and prodrugs thereof, in the manufacture of an antiscarring medicament.
Another aspect of the invention is the use of a compound of formula (I) described herein, and the salts, solvates and prodrugs thereof, in the manufacture of a medicament for the treatment of a PCP-mediated condition or disease.
Another aspect of the invention is a pharmaceutical composition comprising a compound of formula (I), salts thereof, solvates thereof, and/or prodrugs thereof, and a pharmaceutically acceptable diluent, carrier or adjuvant.
Yet another aspect of the Invention Is a method of treatment of a condition mediated by PCP comprising administration of a therapeutically-effective amount of a substance according to the above definitions.
It is to be appreciated that reference to treatment includes prophylaxis as well as the alleviation of established symptoms of PCP-mediated conditions and diseases.

The invention further provides methods for the production of compounds of the invention, which are described below and in the examples and preparations. The skilled man will appreciate that the compounds of the invention could be made by methods other than those specifically described herein, by adaptation of the methods herein described in the sections below and/or adaptation thereof, for example by methods known in the art suitable guides to synthesis, functional group transformations, use of protecting groups, etc. are, for example, "Comprehensive Organic Transformations" by RC Larock, VCH Publishers Inc. (1989), "Advanced Organic Chemistry" by J March, Wiley Interscience (1985), "Designing Organic Synthesise" by S Warren, Wiley Interscience (1978), "Organic Synthesis—The Disconnection Approach" by S Warren, Wiley Interscience (1982), "Guidebook to Organic Synthesis" by RK Mackie and DM Smith, Longman (1982), "Protective Groups in Organic Synthesis"by TW Greene and PGM Wuts, John Wiley and Sons Inc. (1999), and PJ Kocienski, in "Protecting Groups", Georg Thieme Verag (1994), and any updated versions of said standard works.

In the Methods below, unless otherwise specified, the substituents are as defined above with reference to the compounds of formula (I) above.

The compounds of formula (1), where W is N, can be prepared according to the scheme below:

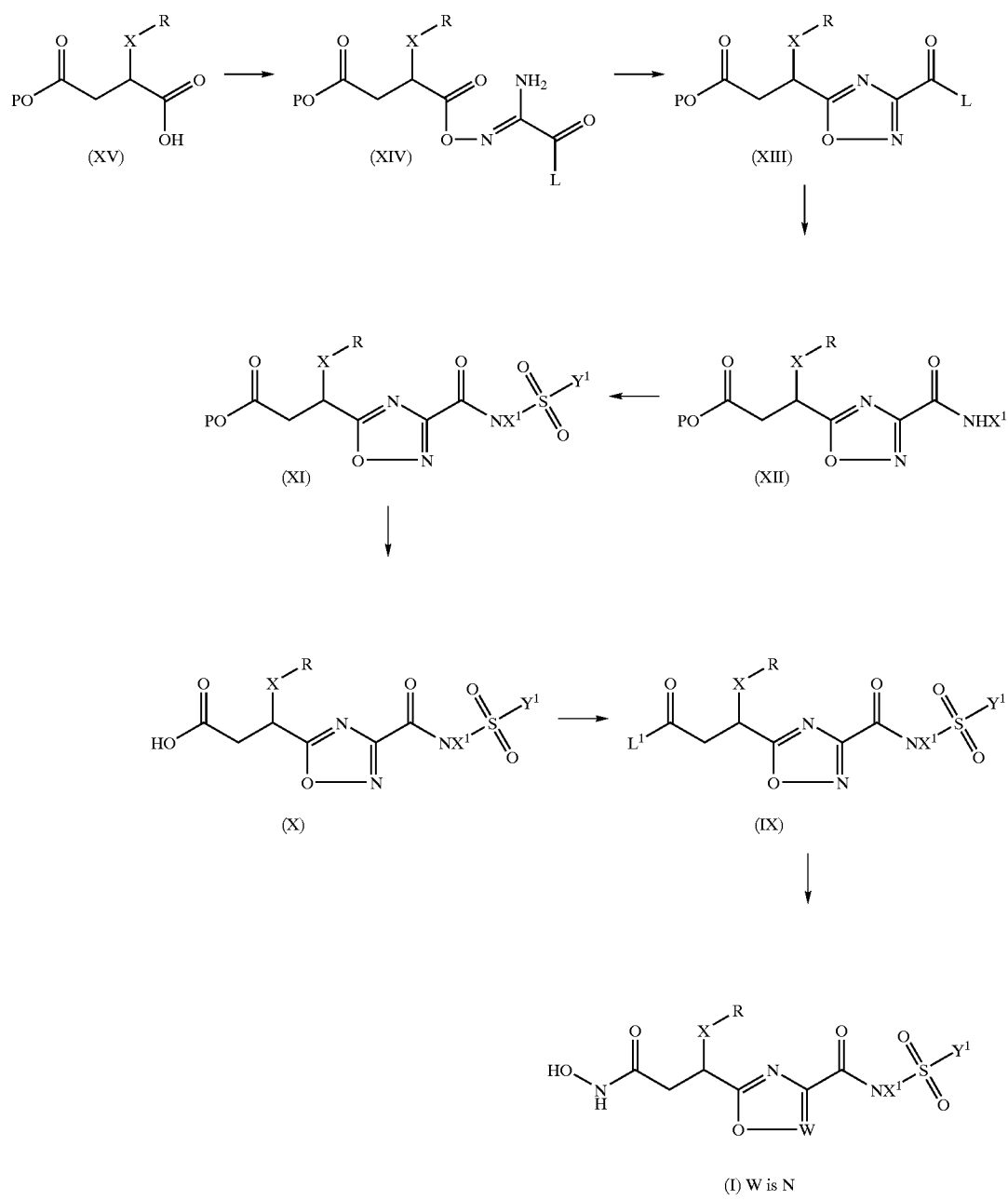

The compounds of formula (I), where W is CZ, can be prepared according to the scheme below:

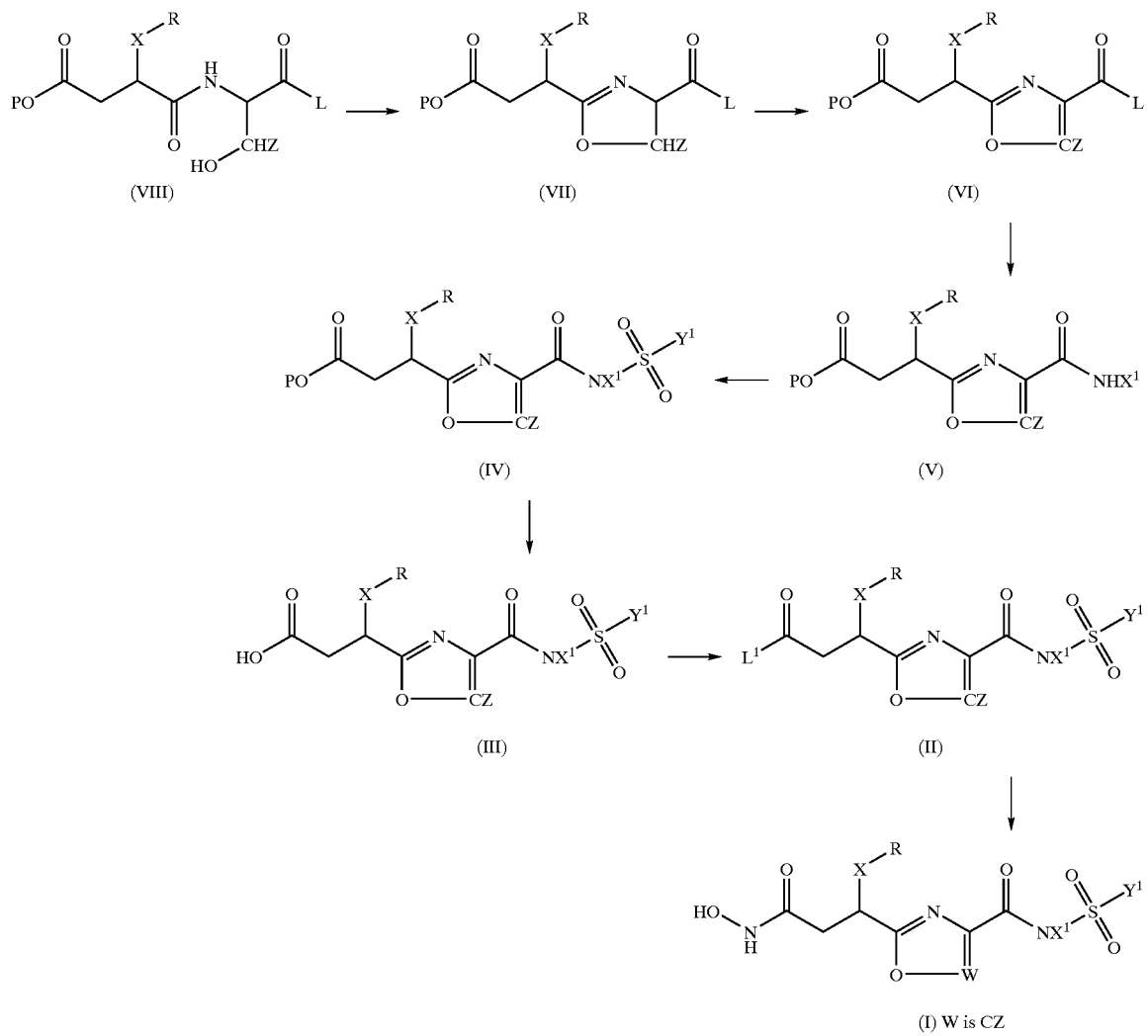

(I) W is CZ

The hydroxamic acid compounds of formula (1) can be made by reaction of the corresponding activated acid derivatives of formula (II) or (IX), where $L^1$ is a suitable leaving group, with hydroxylamine optionally protected with a suitable O-protecting group, such as O-trimethyl silyl group, which can be removed after the substitution reaction with methanol, as illustrated in Example 1.

Suitable leaving groups are generally those which would leave in a more efficient manner than the hydroxide of the parent acids (III) or (X), In a nucleophilic substitution reaction, such as an anhydride, or imidazole. Other suitable leaving groups are familiar to those working in the field of amino acid coupling.

Such compounds of formula (II) or (IX) may be made via standard chemistry from the corresponding acids (X) or (III). Compounds of formula (II) or (IX) where $L^1$ is a leaving group such as anhydride or imidazole and the like, can be made from the corresponding compounds of formula (X) or (111) by conventional methods, including methods typified in e.g. Examples 1, 2 and 10. These examples Illustrate reaction of the acid with an amine base followed by addition of an alkylhaloformate to form a compound of formula (IX) or (II) wherein $L^1$ is alkyl$OCO_2$ leaving group $L^1$, in a suitable solvent such as tetrahydrofuran. Example 3 illustrates the use of a coupling agent such as carbonyldiimidazole to form the imidazolide intermediate, with an imidazole leaving group $L^1$.

Other methods of making hydroxamic acids (I) are known and may be used, e.g. those mentioned in the text by J. March, supra, chapters 0-54, 0-57 and 6-4, and relevant references therein.

Acids of formula (III) or (X) may be made by deprotection of the O-protected species of formula (IV) or (XI). Suitable O-protecting groups can be found in the chapter on O-protection in the book by Greene and Wuts, supra, and include $C_{1-4}$ alkoxy such as t-butoxy, benzyloxy, trialkylsilyloxy such as trimethylsilyloxy, etc.

The deprotection method is determined by the protective group used, as is well known in the art (see Greene and Wuts, supra). E.g. benzyl groups may be removed by hydrogenation, suitably using a catalytic transfer hydrogenation method, t-butyl groups may be removed by treatment with an acid such as trifluoroacetic acid (as typified in Preparation 2), etc.

Compounds of formula (IV) or (XI) can be made by reaction of compounds of formula (V) or (XII), deprotonated if necessary with a base, with a suitable reagent of formula $X^2SO_2Y^1$, where $X^2$ is a suitable leaving group such as chloride or bromid⁻in a nucleophillic substitution reaction, as typified in Preparations 1 and 3.

Compounds of formula (V) and (XII) may be made by addition of an amine of formula $NH_2X^1$ to a compound of formula (VI) or (XII) to displace L, where L Is a suitable leaving group such as methoxy or ethoxy, as exemplified in Preparation 28. Other examples of such standard nucleophillic acyl substitution reactions are well known to those skilled in the art; further examples can be found in references such as: Trost, B. M., Fleming, I., Heathcock, C. H. Comprehensive Organic Synthesis, New York, 1991, vol 6 and Larock, R. C. Comprehensive Organic Transformations, Wiley-VCH, New York, 1999.

Where W=N:

Compounds of formula (XIII), e.g. where P is a t-butoxy group, can be made for example by condensation reaction of a corresponding compound of formula (XIV), for example by heating to elevated temperature in an inert solvent such as in xylene at about 130° C., this reaction being typified by Preparation 27.

Compounds of formula (XIV) can be made for example by coupling an acid of formula (XV) with a reagent of formula $C(NH_2)(COL)=NOH$, which is available via literature methods or adaptation thereof in a conventional manner, such as typified in Preparation 26. Typically the condensation is carried out by adding a solution of the acid (XV) in a suitable inert solvent such as 1,4-dioxane to a suitable agent such as 1-hydroxybenzotriazole hydrate, followed by addition of a suitable coupling agent such as a carbodiimide coupling agent, e.g. N,N'-dicyclohexylcarbodiimide, then treatment with the reagent $C(NH_2)(COL)=NOH$. Suitably the coupling is carried out at ambient temperature.

Compounds of formula (XV) can be made by hydrogenation of the corresponding itaconate derivative, which in turn can be made by conventional methods such as the Stobbe condensation. The preparation of these intermediates is exemplified in Preparation 25.

Where W=CZ:

Compounds of formula (VI), e.g. where P is a t-butoxy group, can be made for example by oxidation of a compound of formula (VII). Suitably the oxidation is carried out using copper (II) bromide with hexamethylenetetramine and a base such as DBU. The reagents, conditions, etc. are typified in Preparation 32 below.

Compounds of formula (VII) may be made by condensation of compounds of formula (VIII), for example by treatment of the compound of formula (VIII) with a suitable agent such as Burgess Reagent, in an anhydrous solvent such as THF, as exemplified in Preparation 31.

Compounds of formula (VIII) may be made by condensation of the add of formula (XV) above with an agent of formula $NH_2CH(COL)CH(Z)OH$, as typified in Preparation 30. Compounds of formula $NH_2CH(COL)CH(Z)OH$ are available commercially, or can be made by methods disclosed in the chemical literature, or by routine modification thereof.

It will be apparent to those skilled in the art that other protection and subsequent deprotection regimes during synthesis of a compound of the invention may be achieved by conventional techniques, for example as described in the volumes by Greene and Wuts, and Kocienski, supra.

Where desired or necessary the compound of formula (I) is converted into a pharmaceutically acceptable salt thereof. A pharmaceutically acceptable salt of a compound of formula (I) may be conveniently be prepared by mixing together solutions of a compound of formula (I) and the desired acid or base, as appropriate. The salt may be precipitated from solution and collected by filtration, or may be collected by other means such as by evaporation of the solvent.

Certain compounds of the Invention may be interconverted into certain other compounds of the invention by methods mentioned in the Examples and Preparations, and well-known methods from the literature.

Compounds of the invention are available by either the methods described herein in the Methods, Examples and Preparations or suitable adaptation thereof using methods known in the art. It is to be understood that the synthetic transformation methods mentioned herein may be carried out in various different sequences in order that the desired compounds can be efficiently assembled. The skilled chemist will exercise his judgement and skill as to the most efficient sequence of reactions for synthesis of a given target compound.

The compounds, salts, solvates (including hydrates) and prodrugs of the invention may be separated and purified by conventional methods.

Separation of diastereomers may be achieved by conventional techniques, e.g. by fractional crystallisation, chromatography or H.P.L.C. of a stereoisomeric mixture of a compound of formula (I) or a suitable salt or derivative thereof. An Individual enantiomer of a compound of formula (I) may also be prepared from a corresponding optically pure intermediate or by resolution, such as by H.P.L.C. of the corresponding racemate using a suitable chiral support or by fractional crystallisation of the diastereomeric salts formed by reaction of the corresponding racemate with a suitably optically active acid or base. In certain cases preferential crystallisation of one of the enantiomers can occur from a solution of a mixture of enantiomers, thus enriching the remaining solution in the other enantiomer.

For human use, the compounds of formula (I) or their salts can be administered alone, but will generally be administered in admixture with a pharmaceutically acceptable diluent or carrier selected with regard to the intended route of administration and standard pharmaceutical practice. For example, they can be administered orally, including sublingually, in the form of tablets containing such excipients as starch or lactose, or in capsules or ovules either alone or in admixture with excipients, or in the form of elixirs, solutions or suspensions containing flavouring or colouring agents. The compound or salt could be incorporated into capsules or tablets for targetting the colon or duodenum via delayed dissolution of said capsules or tablets for a particular time following oral administration. Dissolution could be controlled by susceptibility of the formulation to bacteria found in the duodenum or colon, so that no substantial dissolution takes places before reaching the target area of the gastrointestinal tract. The compounds or salts can be injected parenterally, for example, intravenously, intramuscularly, intradermally or subcutaneously. For parenteral administration, they are best used in the form of a sterile aqueous solution or suspension which may contain other substances, for example, enough salt or glucose to make the solution isotonic with blood. They can be administered topically, or transdermally, in the form of creams, gels, suspensions, lotions, ointments, dusting powders, sprays, foams, mousses, drug-incorporated dressings, solutions, sponges, fibres, microemulsions, films, ointments such as petrolatum or white soft paraffin based ointments or via a skin patch or other device. Penetration enhancers may be used, and the compound may be used in combination with cyclodextrins. In addition, the compound may be delivered using iontophoresis, electroporation, phonophoresis or sonophoresis. They could be administered directly onto a wound site. They could be incorporated into a coated suture. For example they can be incorporated into a lotion or cream consisting of an aqueous or oily emulsion of mineral oils; sorbitan monostearate; polysorbate 60; cetyl esters wax; cetearyl alcohol; 2-octyldodecanol; benzyl alcohol; water; polyethylene glycols and/or liquid paraffin, or they can be incorporated into a suitable ointment consisting of one or more of the following—mineral oil; liquid petrolatum; white petrolatum; propylene glycol, polyoxyethylene polyoxypropylene compound; emulsifying wax and water, or as hydrogel with cellulose or polyacrylate derivatives or other viscosity modifiers, or as a dry powder or liquid spray or aerosol with butane/propane, HFA, CFC, $CO_2$ or other suitable propellant, optionally also including a lubricant such as sorbitan trioleate, or as a drug-incorporated dressing either as a tulle dressing, with white soft paraffin or polyethylene glycols impregnated gauze dressings or with hydrogel, hydrocolloid, alginate or film dressings. The compound or salt could also be administered intraocularly for ophthalmic use e.g. via intraocular injection, or sustained release device, in a lens implant, via subconjunctival injection, or as an eye drop with appropriate buffers, viscosity modifiers (e.g. cellulose or polyacrylate derivatives), preservatives (e.g. benzalkonium chloride (BZK)) and agents to adjust tonicity (e.g. sodium chloride). Such formulation techniques are well-known in the art.

For certain uses, vaginal, rectal and nasal (e.g. by inhalation of a dry powder or aerosol) administration would be suitable.

All such formulations may also contain appropriate stabilisers and preservatives.

The compounds or their salts, solvates or prodrugs may be administered topically by the ocular route. They may be formulated as sterile, isotonic, pH adjusted, buffered suspensions or solutions. A polymer may be added such as crossed-linked polyacrylic acid, polyvinylalcohol, hyaluronic acid, a cellulosic polymer (e.g. hydroxypropylmethylcellulose, hydroxyethylcellulose, methyl cellulose), or a heteropolysaccharide polymer (e.g. gelan gum). Alternatively, they may be formulated in an ointment such as petrolatum or mineral oil, incorporated into biodegradable (e.g. absorbable gel sponges, collagen) or non-biodegradable (e.g. silicone) implants, lenses or delivered via particulate or vesicular systems such as niosomes or liposomes. Formulations may be optionally combined with a preservative, such as benzalkonium chloride. In addition, they may be delivered using iontophoresis. The compound may also be used in combination with cyclodextrins.

An example of preferred formulation excipients of a compound, salt, solvate or prodrug according to the invention:

| Ingredients | % (w/w) composition |
| --- | --- |
| $NaH_2PO_4$ | 0.370 |
| $Na_2HPO_4$ | 0.567 |
| Glycine | 0.430 |
| Carbomer 940 | 1.000 |
| Water | to 100 |
| pH adjusted to ~7 | |

The preferred formulation will be a buffered solution (preferably using monobasic and dibasic sodium phosphate) containing 0.5 to 5.0% of a cross-linked polyacrylic acid, pH adjusted to around 7 with the addition of a stabiliser such as glycine.

For oral and parenteral administration to human patients, the daily dosage level of the compounds of formula (1) or their salts will be from 0.001 to 20, preferably from 0.01 to 20, more preferably from 0.1 to 10, and most preferably from 0.5 to 5 mg/kg (in single or divided doses). Thus tablets or capsules of the compounds will contain from 0.1 to 500, preferably from 50 to 200, mg of active compound for administration singly or two or more at a time as appropriate.

For topical administration to human patients with acute/surgical wounds or scars, the daily dosage level of the compounds, in suspension or other formulation, could be from 0.01 to 50 mg/ml, preferably from 0.3 to 30 mg/ml.

The dosage will vary with the size of the wound, whether or not the wound is open or closed or partially closed, and whether or not the skin is intact.

The physician in any event will determine the actual dosage which will be most suitable for a an individual patient and it will vary with the age, weight and response of the particular patent. The above dosages are exemplary of the average case; there can of course be individual instances where higher or lower dosage ranges are merited, and such are within the scope of this invention.

Biological Test Methods
PCP Inhibition

In order to determine potency of PCP inhibitors a fluorogenic PCP cleavage assay was used. This assay is based on the template of Beekman et al. (FEBS Letters (1996), 390: 221–225) using a fluorogenic substrate. The substrate (Dabcyl-Arg-Tyr-Tyr-Arg-Ala-Asp-Asp-Ala-Asn-Val-Glu (EDANS)—$NH_2$) contains the cleavage site of human PCP (Hojima et al., J Biol Chem (1985), 260: 15996–16003). Human PCP has been purified from supernatant of stable transfected CHO cells using hydrophobic interaction column followed by Superdex 200 gel filtration. 4 µg total protein of this enzyme preparation was incubated with various concentrations of the substance to be tested and $3 \times 10^{-6}$ M substrate in assay buffer (50 mM Tris-Base, pH 7.6 containing 150 mM NaCl, 5 mM $CaCl_2$, 1 µM $ZnCl_2$ and 0.01% Brij 35). The assay was performed in 96-well black fluorimeter plates and fluorescence was read continuously in a fluorimeter over 2.5 hours ($\lambda_{ex}$=340 nm, $\lambda_{em}$=485 nm) at a constant 37° C. with shaking. Release of the fluorogenic signal was in linear correlation to PCP activity. Reading of the mean velocity from 30 min after start of experiment until 2.5 hours was calculated by the Biollose software. $IC_{50}$ values were calculated by plotting % inhibition values against compound concentration using Tessela add in for Excel spreadsheet.

MMP Inhibition

The ability of compounds to inhibit the cleavage of fluorogenic peptides by MMPs 1, 2, 9, and 14 is described below.

The assays for MMPs 2, 9, and 14 are based upon the original protocol described by Knight et al. (Fed. Euro. Biochem. Soc., 296 (3), 263–266; 1992) with the slight modifications given below.

Inhibition of MMP-1
(i) Enzyme Preparation

Catalytic domain MMP-1 was prepared at Pfizer Central Research. A stock solution of MMP-1 (1 µM) was activated by the addition of aminophenylmercuric acetate (APMA), at a final concentration of 1 mM, for 20 minutes at 37° C. MMP-1 was then diluted in Tris-HCl assay buffer (50 mM Tris, 200 mM NaCl, 5 mM $CaCl_2$, 20 µM $ZnSO_4$, 0.05% Brij 35) pH 7.5 to a concentration of 10 nM. The final concentration of enzyme used in the assay was 1 nM.

(ii) Substrate

The fluorogenic substrate used in this assay was Dnp-Pro-□-cyclohexyl-Ala-Gly-Cys(Me)-His-Ala-Lys(N-Me-Ala)-$NH_2$ as originally described by Bickett et al (Anal. Biochem, 212, 58–64, 1993). The final substrate concentration used in the assay was 10 µM.

(iii) Determination of Enzyme Inhibition

Test compounds were dissolved In dimethyl sulphoxide and diluted with assay buffer so that no more than 1% dimethyl sulphoxide was present. Test compound and enzyme were added to each well of a 96 well plate and allowed to equilibrate for 15 minutes at 37° C. in an orbital shaker prior to the addition of substrate. Plates were then incubated for 1 hour at 37° C. prior to determination of fluorescence (substrate cleavage) using a fluorimeter (Fluostar; BMG Lab Technologies, Aylesbury, UK) at an excitaton wavelength of 355 nm and emission wavelength of 440 nm. The potency of inhibitors was measured from the amount of substrate cleavage obtained using a range of test compound concentrations, and, from the resulting dose-response curve, an $IC_{50}$ value (the concentration of inhibitor required to inhibit 50% of the enzyme activity) was calculated.

Inhibition of MMP-2 and MMP-9 (i) Enzyme Preparation

Catalytic domain MMP-2 and MMP-9 were prepared at Pfizer Central Research. A stock solution of MMP-2/MMP-9(1□M) was activated by the addition of aminophenylmercuric acetate (APMA). For MMP-2 and MMP-9, a final concentration of 1 mM APMA was added, followed by incubation for 1 hour at 37° C. The enzymes were then diluted in Tris-HCl assay buffer (100 mM Tris, 100 mM NaCl, 10 mM $CaCl_2$ and 0.16% Brij 35, pH 7.5), to a concentration of 10 nM. The final concentration of enzyme used in the assays was 1 nM.

(ii) Substrate

The fluorogenic substrate used in this screen was Mca-Arg-Pro-Lys-Pro-Tyr-Ala-Nva-Trp-Met-Lys(Dnp)-$NH_2$ (Bachem Ltd, Essex, UK) as originally described by Nagase et al (J. Biol. Chem., 269(33), 20952–20957, 1994). This substrate was selected because it has a balanced hydrolysis rate against MMPs 2 and 9 ($k_{cat}/k_m$ of 54,000, 59,400 and 55,300 $s^{-1}M^{-1}$ respectively). The final substrate concentration used in the assay was 5 $\mu$M.

(iii) Determination of Enzyme Inhibition

Test compounds were dissolved in dimethyl sulphoxide and diluted with test buffer solution (as above) so that no more than 1% dimethyl sulphoxide was present. Test compound and enzyme were added to each well of a 96 well plate and allowed to equilibrate for 15 minutes at 37° C. In an orbital shaker prior to the addition of substrate. Plates were then incubated for 1 hour at 37° C. prior to determination of fluorescence using a fluorimeter (Fluostar; BMG LabTechnologies, Aylesbury, UK) at an excitation wavelength of 328 nm and emission wavelength of 393 nm. The potency of inhibitors was measured from the amount of substrate cleavage obtained using a range of test compound concentrations, and, from the resulting dose-response curve, an $IC_{50}$ value (the concentration of inhibitor required to inhibit 50% of the enzyme activity) was calculated.

Inhibition of MMP-14

(i) Enzyme Preparation

Catalytic domain MMP-14 was purchased from Prof. Tschesche, Department of Biochemistry, Faculty of Chemistry, University of Bielefeld, Germany. A 10□M enzyme stock solution was activated for 20 minutes at 25° C. following the addition of 5□g/ml of trypsin (Sigma, Dorset, UK). The trypsin activity was then neutralised by the addition of 50□g/ml of soyabean trypsin inhibitor (Sigma, Dorset, UK), prior to dilution of this enzyme stock solution in Tris-HCl assay buffer (100 mM Tris, 100 mM NaCl, 10 mM $CaCl_2$ and 0.16% Brij 35, pH 7.5) to a concentration of 10 nM. The final concentration of enzyme used In the assay was 1 nM.

(ii) Substrate

The fluorogenic substrate used in this screen was Mca-Pro-Leu-Gly-Leu-Dpa-Ala-ArgNH2 (Bachem Ltd, Essex, UK) as described by Will et al (J. Biol. Chem., 271(29), 17119–17123, 1996). The final substrate concentration used in the assay was 10 $\mu$M.

Determination of enzyme inhibition by test compounds was performed in the same manner as described for MMPs-2 and -9 above.

The compounds of Examples 1–12 had PCP $IC_{50}$ values of 100 $\mu$M and below.

All references mentioned herein in this text are incorporated by reference in their entirety.

EXAMPLES AND PREPARATIONS

Melting points were determined using open glass capillary tubes and a Gallenkamp melting point apparatus and are uncorrected. Nuclear magnetic resonance (NMR) data were obtained using Varian Unity Inova-400, Varian Unity Inova-300 or Bruker AC300 spectrometers and are quoted in parts per million from tetramethylsilane. Mass spectral (MS) data were obtained on a Finnigan Mat. TSQ 7000 or a Fisons Instruments Trio 1000. The calculated and observed ions quoted refer to the isotopic composition of lowest mass. Infra red (1R) spectra were measured using a Nicolet Magna 550 Fourier transform infra-red spectrometer. Flash chromatography refers to column chromatography on silica gel (Kieselgel 60,230–400 mesh, from E. Merck, Darmstadt. Kieselgel 60 Fs plates from E. Merck were used for TLC, and compounds were visualised using UV light, 5% aqueous potassium permanganate or Dragendorff's reagent (oversprayed with aqueous sodium nitrite). Thermal analyses by Differential Scanning Calorimetry (DSC) and ThermoGravimetric Analysis (TGA) were obtained using Perkin Elmer DSC7 and TGA7. Moisture sorption characteristics were recorded using Surface Measurement Systems Ltd. Automated Water Sorption Analyser DVS 1. Water content was determined on a Mitsubishi CA100 (Coulometric Karl Fisher Titrator). Powder X-ray diffraction (PXRD) pattern was determined using a Siemens D5000 powder X-ray diffractometer fitted with an automatic sample changer, a theta—theta gonlometer, automatic beam divergence slits, a secondary monochromator and a scintillation counter. Other measurements were taken using standard equipment. Hexane refers to a mixture of hexanes (hplc grade) b.p. 65–70° C. Ether refers to diethyl ether. Acetic acid refers to glacial acetic acid. 1-Hydroxy-7-aza-1H-1,2,3-benzotriazole (HOAt), N-[[(dimethylamino)-1H-1,2,3-triazolo[4,5-b]pyridin-1-ylmethylene]-N-methylmethaninIum hexafluorophosphate N-oxide (HATU) and 7-azabenzotriazol-1-yloxytris(pyrrolidino)phosphonium hexafluorophosphate (PyAOP) were purchased from PerSeptive Biosystems U.K. Ltd. "DIPE" refers to diisopropyl ether. Reverse-phase silica gel for flash chromatography was obtained from Fluka (Fluka 100, $C_{18}$, 40–63 $\mu$). Pentane refers to High Performance Liquid Chromatography (HPLC) grade n-pentane (b.pt.35–37° C.). Nomenclature has been allocated using a program available from IUPAC. Standard abbreviations are used throughout, e.g. "Me" is methyl, "Et" is ethyl, "Pr" is propyl, "Ph" is phenyl, etc. It was noticed that during certain repetitions of the methods disclosed in the Examples and Preparations that some racemisation appeared to have taken place. It was found in some cases that specific desired enantiomers can be separated from mixtures thereof by routine methods such as by differential crystallisation.

[a]HPLC autopurification performed using 2 columns—Phenomenex LUNA CB 150×21.2 mm, 10 $\mu$m and Phenomenex MAGELLEN C18 150×21.2 mm, 5 $\mu$m, eluting ith a gradient system of organic solvent ammonium acetate (aq) 100 mM: acetonitrile (1:9)): aqueous solvent [ammonium acetate (aq) 100 mM: acetonitrile (9:1)]

[b]HPLC autopurification performed using 2 columns—Phenomenex LUNA CB 150×21.2 mm, 10 $\mu$m and Phenomenex MAGELLEN Cia 150×21.2 mm, 5 $\mu$m, eluting with a gradient system of organic solvent (acetonitrile): aqueous solvent (0.1% aqueous trifluoroacetic acid)

Example 1
(3R)-6-Cyclohexyl-N-hydroxy-3-(3-{[(phenylsulfonyl)amino]carbonyl}-1,2,4-oxadiazol-5-yl)hexanamide

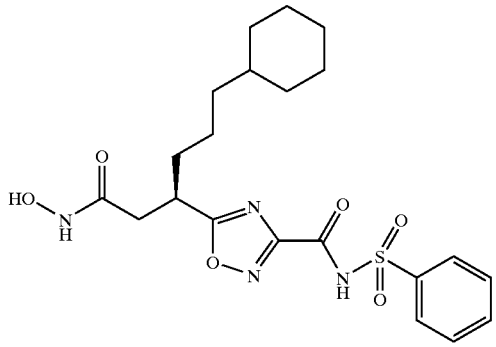

To a solution of the title compound from Preparation 2 (2.24 g, 5.0 mmol) in THF (40 mL) was added 2,6-lutidine (1.07 g, 10.0 mmol), the solution was cooled to ° C. and then iso-butylchloroformate (0.66 mL, 5.05 mmol) was added. The reaction was stirred at 0° C. for 1 hour then O-trimethylsilyl hydroxylamine (1.83 mL, 15.0 mmol) was added, the reaction was warmed to room temperature and stirred overnight. Methanol (25 mL) was added, and stirring was continued for 30 minutes. The solvent was removed in vacuo and the residue was then partitioned between ethyl acetate (75 mL) and 2M aqueous hydrochloric acid (35 mL). The layers were separated and the aqueous layer was extracted with ethyl acetate (60 mL). The combined organic extracts were dried ($Na_2SO_4$) and the solvent was removed in vacuo. The residue was dissolved in water/acetonltrile and purified by chromatography on a Biotage CP-18 reverse phase 40S cartridge (graded elution of acetonitrile/water 30:70 to 50:50) to give a white foam which was recrystallised from toluene to give the title compound as a white crystalline solid (1.0 g).
Mpt 80–90° C.
$^1$H NMR (400 MHz, $D_6$-DMSO) □0.74–0.89 (m, 2H), 1.06–1.24 (m, 8H), 1.53–1.69 (m, 7H), 2.66–2.81 (m, 2H), 3.39–3.47 (m, fH), 7.52–7.69 (m, 3H), 7.94 (d, 2H), 8.05 (s, 1H), 10.9–11.4 (br s, 2H).
LRMS (ES) 487 (M+Na).
Anal. Calcd. For $C21H_{28}N_4O_6S$+0.15 $CH_2Cl_2$+0.2 toluene: calc C=50.94, F=6.43, N=10.54, found C=51.04, H=6.05, N=10.45.

Example 2
(3R)-6-Cyclohexyl-N-hydroxy-3-[3-({[(4-methylphenyl)sulfonyl]amino}carbonyl)-1,2,4-oxadiazol-5-yl]hexanamide

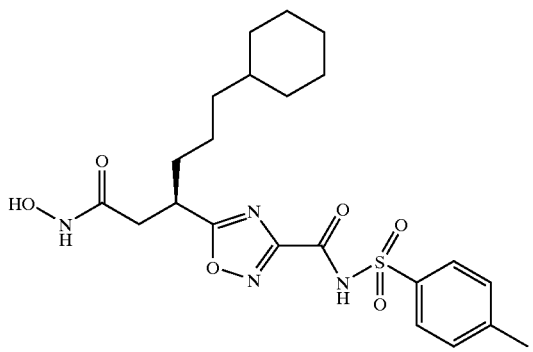

To a solution of the title compound from Preparation 4 (0.23 g, 0.5 mmol) in THF (12 mL) was added triethylamine (0.14 mL, 1.0 mmol). The reaction was cooled to 0° C. in an ice bath, then iso-butylchloroformate (0.06 mL, 0.5 mmol) was added and a precipitate began to form immediately. The mixture was stirred for 1 hour, then O-trimethylsilyl hydroxylamine (0.20 mL, 1.6 mmol) was added and the reaction was warmed to room temperature and stirred overnight. Methanol (10 mL) was added, stirring was continued for 1.5 hours, and then the solvent was removed in vacuo. The residue was dissolved in ethyl acetate (50 mL) and washed with water (50 mL). The organic layer was dried ($MgSO_4$) and the solvent was evaporated in vacuo. The residue was purified by flash chromatography on silica gel (graded elution with dichloromethane/methanol/glacial acetic add 99:1:0.1 to 98:2:0.2 to 95:5:0.5 to 90:10:1) to give the title compound as an orange foam which was azeotroped with toluene to remove traces of acetic acid (0.067 g).
Mpt 82–84° C.
$^1$H NMR (400 MHz, $D_6$-DMSO)□0.72–0.84 (m, 2H), 1.05–1.20 (m, 8H), 1.53–1.75 (m, 7H), 2.36 (s, 3H), 2.38–2.53 (m, 2H), 3.40–3.49 (m, 1H), 7.37 (d, 2H), 7.71 (d, 2H), 10.37 (s,1H).
LRMS (ES) 477 (M-H).
Anal. Calcd. For $C^{22}H_{30}N_4O_6S$+0.2 $CH_2Cl_2$+0.1 PhMe: C, 54.49; H, 6.23; N, 11.10. Found C, 54.35; H, 6.37; N. 10.95.

Example 3
3R)-6-Cyclohexyl-N-hydroxy-3[3-({[(4-methoxyphenyl)sulfonyl]amino}carbonyl)-1,2,4-oxadiazol-5-yl]hexanamide

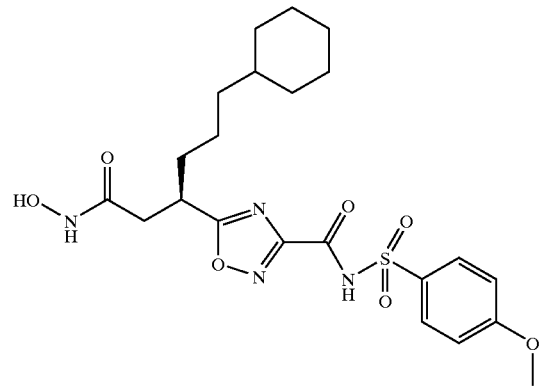

To a solution of the title compound from Preparation 6 (0.25 g, 0.5 mmol) in THF (5 mL) was added 1,1-carbonyldiimidazole (0.093 g, 0.6 mmol). The mixture was stirred for 1 hour, then O-trimethylsilyl hydroxylamine (0.19 mL, 1.6 mmol) was added and the reaction was stirred at room temperature overnight. Methanol (10 mL) was added, stirring was continued for 1 hour and then the solvent was removed in vacuo. The residue was purified by flash chromatography on a Biotage 401 flash system (dichloromethane/methanol/glacial acetic acid 90:10:1.0 as eluant) to give an orange foam which was triturated with diisopropyl ether. The solid was collected by filtration and dried to give the title compound as an orange solid (0.35 g).
Mpt 55–62° C.
$^1$H NMR (400 MHz, $D_6$-DMSO)□0.73–0.82 (m, 2H), 1.00–1.20 (m, 8H), 1.50–1.77 (m, 7H), 2.38–2.53 (m, 2H), 3.37–3.49 (m, 1H), 3.80 (s, 3H), 7.07 (d, 2H), 7.86 (d, 2H), 10.40 (s, 1H).
LRMS (ES) 493 (M-H).
Anal. Calcd. For $C_{22}H_{30}N_4O_6S$+0.4$H_2O$: C, 52.66; H, 6.19; N, 11.17. Found C, 52.77; H. 6.26; N, 11.09.

Example 4

(3R)-6-Cyclohexyl-3-(3({[(4-fluorophenyl)sulfonyl]amino}carbonyl)-1,2,4-oxadiazol-5-yl]-N-hydroxyhexanamide

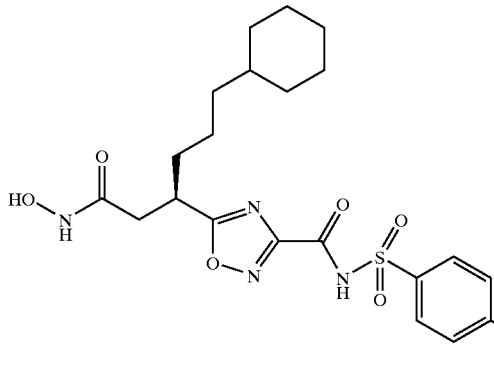

The title compound was obtained as a white foam from the title compound from Preparation 8, using a similar method to that described In Example 2.

$^1$H NMR (400 MHz, D$_6$-DMSO) □0.72–0.84 (m, 2H), 1.03–1.20 (m, 8H), 1.52–1.65 (m, 7H), 2.38–2.52 (m, 2H), 3.363.47 (m, 1H), 7.30 (m, 2H), 7.92 (m, 2H), 10.37 (s, 1H).

LRMS (ES) 481 (M−H).

Anal. Calcd. For C$_{21}$H$_{27}$FN$_4$O$_6$S+0.7H$_2$O: C, 50.94; H, 5.78; N, 11.32. Found C, 50.91; H, 5.69; N, 11.32.

Example 5

(3R)-6-Cyclohexyl-N-hydroxy-3-[3-({[(4-isopropylphenyl)sulfonyl]amino} carbonyl)-1,2,4-oxadiazol-5-yl] hexanamide

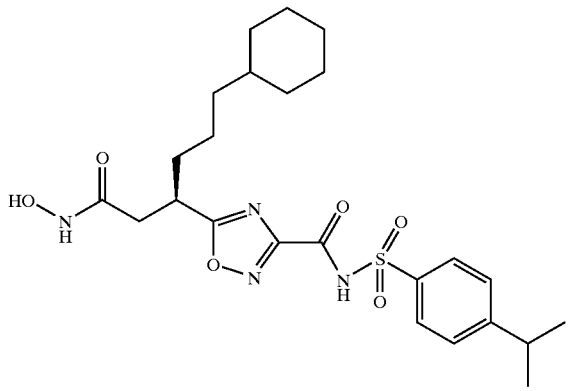

The title compound was obtained as a white foam from the title compound from Preparation 10, using a similar method to that described in Example 2.

$^1$H NMR (400 MHz, D-DMSO) □0.72–0.83 (m, 2H), 1.02–1.24 (m, 8H), 1.21 (d, 6H), 1.52–1.65 (m, 7H), 2.392.52 (m, 2H), 2.94–3.01 (m, 1H), 3.41–3.50 (m, 1H), 7.47 (d, 2H), 7.78 (d, 2H), 10.37 (s, 1H).

LRMS (ES) 505 (M−H).

Anal. Calcd. For C$_{24}$H$_{34}$N$_4$O$_6$S+0.4H$_2$O: C, 56.10; H, 6.83; N, 10.90. Found C, 56.28; H, 6.91; N, 10.70.

Example 6

(3R)-6-Cyclohexyl-3-[3-({[(3,4-dimethoxyphenyl)sulfonyl]amino}carbonyl)-1,2,4-oxadiazol-5-yl]-N-hydroxyhexanamide

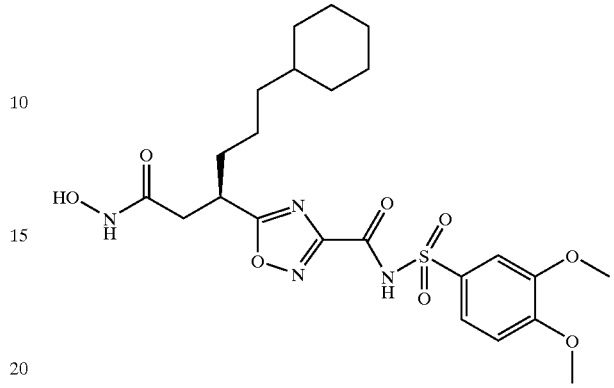

The title compound was obtained as an orange foam from the title compound from Preparation 12, using a similar method to that described in Example 3.

$^1$H NMR (400 MHz, D$_6$-DMSO) □0.71–0.85 (m, 2H), 1.04–1.22 (m, 8H), 1.52–1.67 (m, 7H), 2.40–2.53 (m, 2H), 3.41–3.49 (m, 1H), 3.80 (s, 3H), 3.82 (s, 3H), 7.13 (d, 1H), 7.46 (s, 1H), 7.54 (d, 1H), 10.36 (s, 1H).

LRMS (ES) 523 (M−H).

Anal. Calcd. For C$_{23}$H$_{32}$N$_4$O$_8$S: C, 52.66; H, 6.15; N, 10.68. Found C, 52.31; H, 6.30; N, 10.39.

Example 7

(3R)-6-Cyclohexyl-N-hydroxy-3-(3-{[(8-quinolinylsulfonyl)amino]carbonyl}-1,2,4-oxadiazol-5-yl) hexanamide

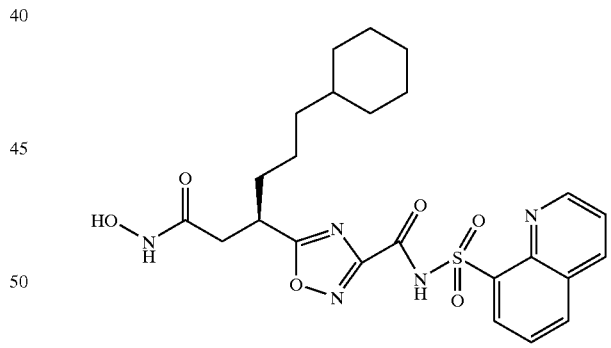

The title compound was obtained as a white solid from the title compound from Preparation 14, using a similar method to that described in Example 1.

Mpt 155–158° C.

$^1$H NMR (400 MHz, D$_6$-DMSO) □0.72–0.86 (m, 2H), 1.02–1.22 (m, 8H), 1.50–1.68 (m, 7H), 2.34–2.53 (m, 2H), 3.33–3.44 (m, 1H), 7.53 (dd, 1H), 7.66 (dd, 1H), 8.07 (d, 1H), 8.32–8.41 (m, 2H), 8.63 (s, 1H), 8.88–8.94 (m, 1H), 10.36 (s, 1H).

LRMS (ES) 514 (M−H).

Anal. Calcd. For C$_{24}$H$_{29}$N$_5$O$_6$S+1.3H$_2$O: C, 53.48; H, 5.91; N, 12.99. Found C, 53.10; H, 5.72; N, 12.80.

Example 8

(3R)-6-Cyclohexyl-3-[3-({[(3,5-dimethyl-4-isoxazolyl)sulfonyl]amino}carbonyl)-1,2,4-oxadiazol-5-yl]-N-hydroxyhexanamide

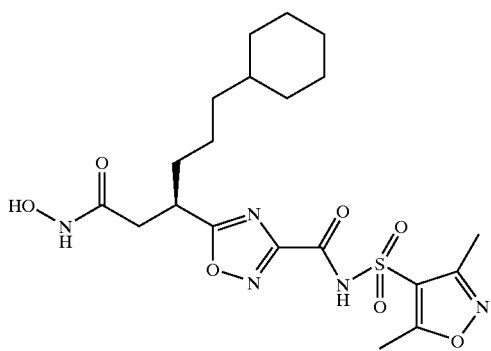

The title compound was obtained as an orange solid from the title compound from Preparation 16, using a similar method to that described in Example 1.

Mpt 122–124° C.

$^1$H NMR (400 MHz, D$_6$-DMSO)□0.73–0.85 (m, 2H), 1.03–1.22 (m, 8H), 1.51–1.68 (m, 7H), 2.26 (s, 3H), 2.38–2.50 (m, 2H), 2.52 (s, 3H), 3.34–3.44 (m, 1H), 9.63 (s, 1H), 10.35 (s, 1H).

LRMS (ES) 482 (M-H).

Anal. Calcd. For C$_{20}$H$_{29}$N$_5$O$_7$S+1.6H$_2$O: C, 46.88; H, 6.33; N, 13.39. Found C, 46.57H, 5.89; N, 13.33.

Example 9

3R)-6-Cyclohexyl-N-hydroxy-3-(3-{[(isopropylsulfonyl)amino]carbonyl}-1,2,4-oxadiazol-5-yl)hexanamide

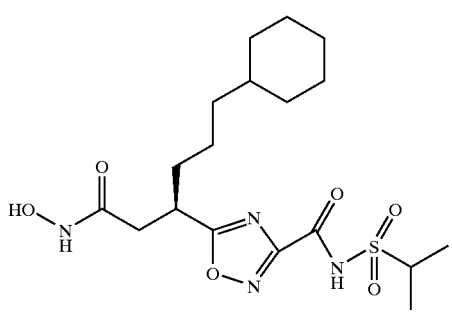

The title compound was obtained as an orange solid from the title compound from Preparation 18, using a similar method to that described in Example 3, apart from the final compound was azeotroped with toluene to remove traces of acetic acid.

$^1$H NMR (400 MHz, D$_6$-DMSO)□0.73–0.87 (m, 2H), 1.03–1.23 (m, 14H), 1.51–1.67 (m, 7H), 2.38–2.50 (m, 2H), 3.32–3.48 (m, 2H), 8.62 (s, 1H), 10.38 (s, 1H).

LRMS (ES) 429 (M-H).

Anal. Calcd. For C$_{18}$H$_{30}$N$_4$O$_6$S+0.08H$_2$O+1.28 CH$_2$Cl$_2$:C, 42.83; H, 6.10; N, 10.36. Found C, 42.44; H, 5.79; N, 10.76.

Example 10

(3R)-6-Cyclohexyl-N-hydroxy-3-(3-{[methyl(methylsulfonyl)amino]carbonyl}-1,2,4-oxadiazol-5-yl]hexanamide

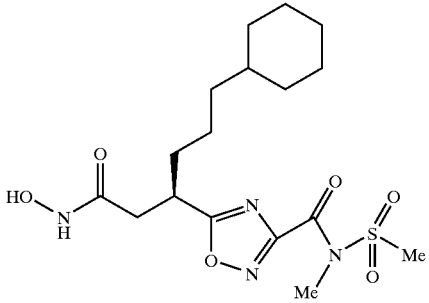

To a solution of the title compound from Preparation 20 (0.22 g, 0.54 mmol) in tetrahydrofuran (6 mL) and diethyl ether (6 mL) at 0° C. was added N-methylmorpholine (0.065 mL, 0.59 mmol) followed by ethyl chloroformate (0.057 mL, 0.59 mmol). The reaction was stirred for 1 hour then aqueous hydroxylamine (0.076 mL of a 50% w/v solution, 1.3 mmol) was added. The reaction was slowly warmed to room temperature over 2 hours and then the solvents were removed in vacuo. The residue was taken up in ethyl acetate (10 mL) and washed with 6M aqueous hydrochloric acid solution (10 mL), water (10 mL) then saturated aqueous sodium chloride solution (10 mL). The organic layer was dried (Na$_2$SO$_4$) and the solvent removed in vacuo. The residue was purified by flash chromatography on silica gel (graded elution of dichloromethane/methano/acetic acid 195:5:1 to 190:10:1), and the azeotroped with toluene to remove traces of acetic acid to give the title compound as a white foam (0.050 g).

$^1$H NMR (400 MHz, D$_6$-DMSO)□0.73–0.86 (m, 2H), 1.02–1.23 (m, 8H), 1.53–1.74 (m, 7H), 2.38–2.50 (m, 2H), 3.27 (s, 3H), 3.463.58 (m, 4H), 8.63 (s, 1H), 10.39 (s, 1H).

LRMS (ES) 439 (M+Na).

Anal. Calcd. For C$_{17}$H$_{28}$N$_4$O$_6$S+0.09 CH$_2$Cl$_2$+0.09 PhMe: C, 49.22; H, 6.74; N. 12.96. Found C, 49.17H, 6.85; N, 12.82.

Example 11

(3R)-6-Cyclohexyl-N-hydroxy-3-(3-{[(phenylmethyl)sulfonyl]amino}carbonyl)-1,2,4-oxadiazol-5-yl)hexanamide

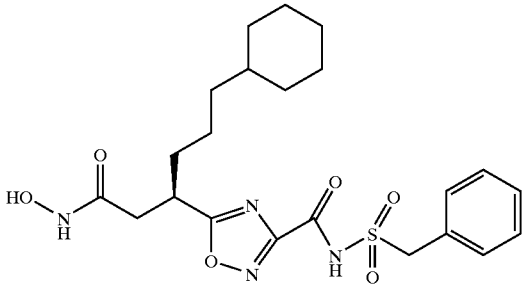

The title compound was obtained as an orange solid from the title compound from Preparation 22, using a similar method to that described in Example 3, apart from the final compound was purified by flash chromatography on silica gel (elution with dichloromethane/methano/acetic acid 188:12:1) and then azeotroped with toluene to remove traces of acetic acid.

$^1$H NMR (400 MHz, CDCl$_3$)□0.73–0.87 (m, 2H), 1.01–1.22 (m, 8H), 1.51–1.77 (m, 7H), 2.38–2.50 (m, 2H), 3.40 (m, 1H), 4.34 (s, 2H), 7.17–7.33 (m, 5H), 8.64 (s, 1H), 10.37 (s, 1H).

LRMS (ES) 477 (M−H).
HRMS (ES) 501 (M+Na). Calcd. For $C_{22}H_{30}N_4O_8S$+Na: 501.1778. Found 501.1767.

Example 12
(3R)-6-Cyclohexyl-N-hydroxy-3-(3-{[(3-pyridylsulfonyl)amino]carbonyl)-1,2,4-oxadiazol-5-yl)hexanamide

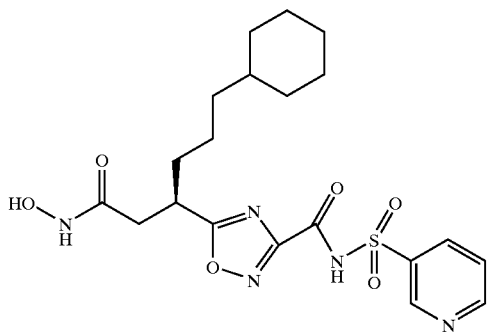

The title compound was obtained as an orange solid from the title compound from Preparation 24, using a similar method to that described in Example 3, apart from the final compound was purified by flash chromatography on silica gel (graded elution of dichloromethane/methanol/acetic acid 195:5:1 to 190:10:1) and then azeotroped with toluene to remove traces of acetic acid.

$^1$H NMR (400 MHz, $D_6$-DMSO) p0.700.85 (m, 2H), 1.01–1.24 (m, 8H), 1.481.78 (m, 7H), 2.38–2.50 (m, 2H), 3.39 (m, 1H), 7.49 (m, 1H), 8.10 (d, 1H), 8.62 (d, 1H), 8.96 (s, 1H), 10.36 (s, 1H).
LRMS (ES) 464 (MH).

Preparation 1
tert-Butyl (3R)-6-cyclohexyl-3-(3-{[(phenylsulfonyl)amino]carbonyl}-1,2,4-oxadiazol-5-yl)hexanoate

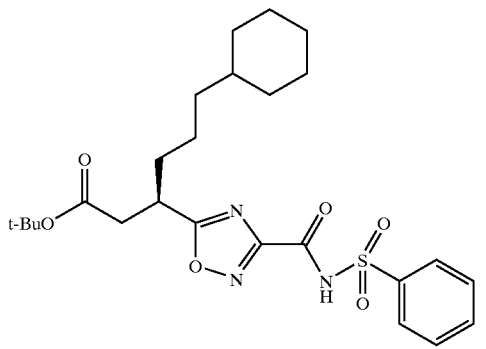

To a suspension of sodium hydride (0.65 g of 60% dispersion in mineral oil, 16.4 mmol) in tetrahydrofuran (80 mL) at 0° C. was added a solution of the title compound from Preparation 28 (3.0 g, 8.2 mmol) and freshly distilled benzenesulfonyl chloride (1.15 mL, 9.0 mmol) in tetrahydrofuran (20 mL) dropwise. The reaction was stirred at 0° C. for 3 hours then quenched with 2M aqueous hydrochloric acid and warmed to room temperature. The mixture was diluted with water (50 mL) and then extracted with ethyl acetate (3×100 mL). The combined organic extracts were dried ($Na_2SO_4$) and the solvent was removed in vacuo. The residue was purified by flash chromatography on a Biotage 405 cartridge (graded elution of dichloromethane to dichloromethane/methanol 95:5) to give the title compound as a clear oil (2.6 g).

$^1$H NMR (400 MHz, $CDCl_3$) □0.78–0.91 (m, 2H), 1.11–1.55 (m, 18H), 1.55–1.79 (m, 6H), 2.65 (dd, 1H), 2.80 (dd, 1H), 3.44–3.52 (m, 1H), 7.56 (dd, 2H), 7.66 (dd, 1H), 8.17 (d, 2H).

LRMS (ES) 504 (M−H).
Anal. Calcd. For $C_{25}H_{35}N_3O_6S$+0.5$H_2O$: C, 58.35; H, 7.05; N, 8.16. Found C, 58.49; H, 6.93; N, 8.16.

Preparation 2
(3R)-6-Cyclohexyl-3-(3-{[(phenylsulfonyl)amino]carbonyl}-1,2,4-oxadiazol-5-yl)hexanoic acid

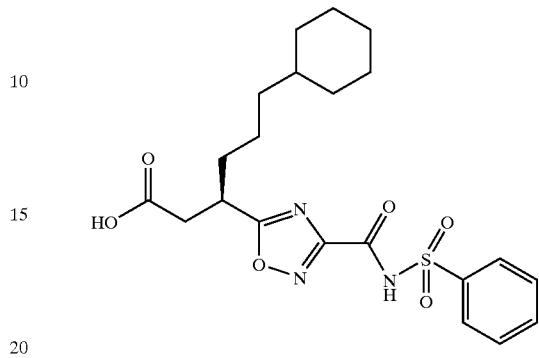

The title compound from Preparation 1 (2.65 g, 1.0 mmol) was dissolved in dichloromethane (30 mL) then trifluoroacetic acid (6 mL) was added and the reaction was stirred at room temperature for 2 hours. A further portion of trifluoroacetic acid (1 mL) was added and stirring was continued for 1 hour. The solvent was removed in vacuo, and the residue was azeotroped with toluene (3 times) to remove traces of trifluoroacetic acid, to give the title compound as a viscous oil (2.28 g).

$^1$H NMR (400 MHz, $D_6$-DMSO)□0.72–0.85 (m, 2H), 1.01–1.26 (m, 8H), 1.52–1.69 (m, 7H), 2.67–2.81 (m, 2H), 3.39–3.50 (m, 1H), 7.56–7.68 (m, 2H), 7.68–7.76 (m, 1H), 7.97 (d, 2H).
LRMS (ES) 448 (M−H).

Preparation 3
tert-Butyl (3R)$_4$-cyclohexyl-3[3-({[(4-methylphenyl)sulfonyl]amino}carbonyl)-1,2,4-oxadiazol-5-yl]hexanoate

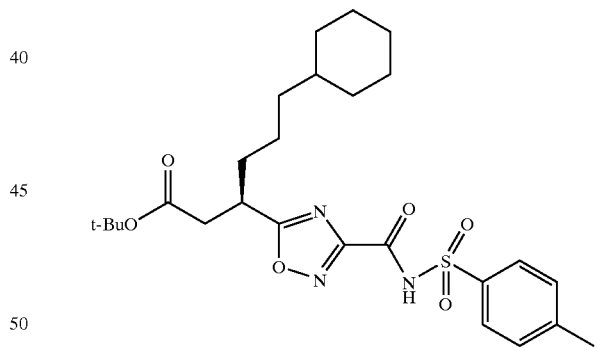

To a suspension of sodium hydride (0.19 g of 60% dispersion in mineral oil, 4.8 mmol) in tetrahydrofuran (30 mL) at 0° C. was added a solution of the title compound from Preparation 28 (0.80 g, 2.2 mmol) and p-toluenesulfonyl chloride (0.46 g, 2.4 mmol) in tetrahydrofuran (20 mL) dropwise. The reaction was stirred at 0° C. for 1 hour then warmed to room temperature and stirred overnight. Saturated aqueous ammonium chloride solution was added, the pH was adjusted to 3 with 2M aqueous hydrochloric acid solution and then extracted with dichloromethane (3×50 mL). The combined organic extracts were dried (MgSO4) and, the solvent was removed in vacuo. The residue was purified by flash chromatography on silica gel (graded elution of pentane/dichloromethane 3:1 to 2:1 to 1:1 to 100% dichloromethane to dichloromethane/methanol 98:2) to give the title compound as a clear oil (0.40 g).

¹H NMR (400 MHz, D₆-DMSO) □0.71–0.84 (m, 2H), 1.03–1.25 (m, 8H), 1.27 (s, 9H), 1.53–1.66 (m, 7H), 2.38 (s, 3H), 2.62.72 (m, 2H), 3.39–3.46 (m, 1H), 7.42 (d, 2H), 7.85 (d, 2H).

LRMS (ES) 518 (M−H).

Anal. Calcd. For $C_{26}H_{37}N_3O_6S+0.6H_2O$: C, 58.87; H. 7.26; N, 7.92. Found C, 58.66; H, 7.01; N, 7.70.

Preparation 4

(3R)-6-Cyclohexyl-3-[3-({[(4-methylphenyl)sulfonyl]amino}carbonyl)-1,2,4-oxadiazol-5 yl]hexanoic acid

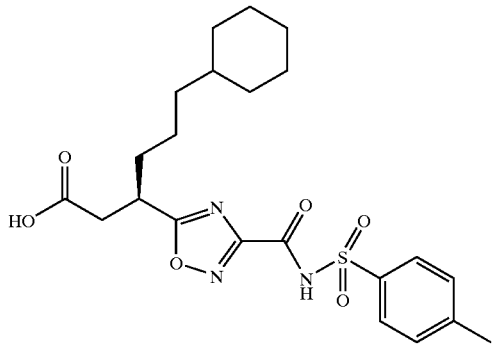

Hydrogen chloride gas was bubbled through dichloromethane (10 mL) until the solution was saturated, then the title compound from Preparation 3 (0.40 g, 0.8 mmol) was added and the reaction was stirred at room temperature overnight. More hydrogen chloride gas was bubbled through the reaction mixture, then stirring was continued for another 4 hours. The reaction was not complete, so trifluoroacetic acid (1.0 mL) was added and the reaction was stirred overnight. The solvent was removed in vacuo and azeotroped with toluene, to give the title compound as a clear oil (0.24 g).

¹H NMR (400 MHz, D₆-DMSO) □0.72–0.85 (m, 2H), 1.01–1.25 (m, 8H), 1.51–1.70 (m, 7H), 2.37 (s, 3H), 2.65–2.72 (m, 2H), 3.36–3.48 (m, 1H), 7.40 (d, 2H), 7.85 (d, 2H).

LRMS (ES) 462 (M−H).

Anal. Calcd. For $C_{22}H_{29}N_3O_6S+0.2$ DIPE+$0.3H_2O$: C, 56.94; H, 6.67; N, 8.59. Found C, 56.91; H, 6.64; N, 8.39.

Preparation 5 tert-Butyl (3R)-6-cyclohexyl-3-[3-({[(4-methoxypheny)sulfonyl]amino}carbonyl)-1,2,4-oxadiazol-5-yl]hexanoate

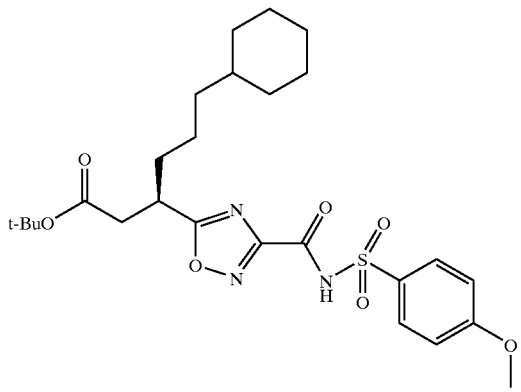

The title compound was obtained as a white foam from the title compound from Preparation 28 and 4-methoxybenzenesulfonyl chloride, using a similar method to that described in Preparation 3.

¹H NMR (400 MHz, D₆-DMSO) □0.71–0.84 (m, 2H), 1.03–1.25 (m, 8H), 1.27 (s, 9H), 1.52–1.69 (m, 7H), 2.67–2.74 (m, 2H), 3.38–3.48 (m, 1H), 3.84 (s, 3H), 7.13 (d, 2H), 7.90 (d, 2H).

LRMS (ES) 534 (M−H).

Anal. Calcd. For $C_{26}H_{37}N_3O_7S$: C, 58.30; H, 6.96; N, 7.84. Found C, 58.20; H. 7.02; N, 7.76.

Preparation 6

(3R)-6-Cyclohexyl-3-[3-({[(4-methoxyphenyl)sulfonyl]amino}carbonyl)-1,2,4-oxadiazol-5-yl]hexanoic acid

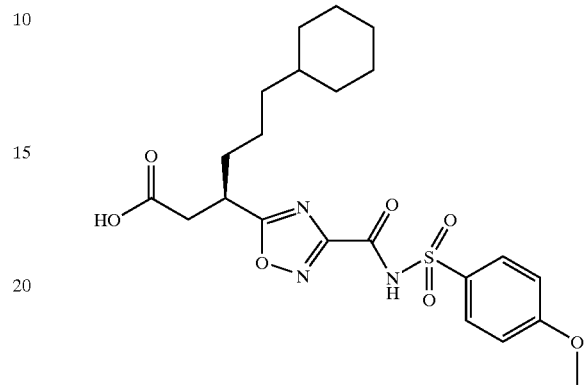

The title compound from Preparation 5 (0.55 g, 1.0 mmol) was dissolved in dichloromethane, then trifluoroacetic acid (1 mL) was added and the reaction was stirred at room temperature overnight. A further 1 mL of trifluoroacetic acid was added and stirring was continued for 4 hours. The solvent was then removed in vacuo and azeotroped with toluene to give the title compound as a white solid (0.50 g).

Mpt 123–127° C.

¹H NMR (400 MHz, D₆-DMSO) □0.73–0.85 (m, 2H), 1.03–1.24 (m, 8H), 1.52–1.68 (m, 7H), 2.67–2.80 (m, 2H), 3.38–3.48 (m, 1H), 3.84 (s, 3H), 7.12 (d, 2H), 7.91 (d, 2H).

LRMS (ES) 478 (M−H).

Anal. Calcd. For $C_{22}H_{29}N_3O_7S$: C, 55.10; H, 6.10; N, 8.76. Found C, 55.29; H, 6.07; N, 8.71.

Preparation 7 tert-Butyl (3R)-6-cyclohexyl-3-[3-({[(4-fluorophenyl)sulfonyl]amino}carbonyl)-1,2,4-oxadiazol-5-yl]hexanoate

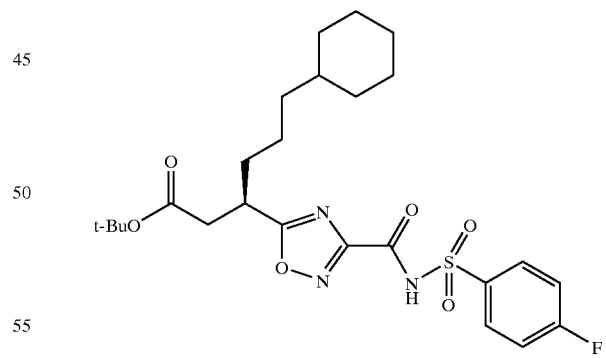

The title compound was obtained as a white foam from the title compound from Preparation 28 and 4-fluorobenzenesulfonyl chloride, using a similar method to that described in Preparation 1.

¹H NMR (400 MHz, D₆-DMSO) □0.71–0.84 (m, 2H), 1.03–1.32 (m, 17H), 1.52–1.69 (m, 7H), 2.67–2.77 (m, 2H), 3.38–3.46 (m, 1H), 7.42 (m, 2H), 8.03 (m, 2H).

LRMS (ES) 522 (M−H).

Anal. Calcd. For $C_{25}H_{34}FN_3O_6S+0.25$ $CH_2Cl_2$: C, 55.66; H, 6.38; N, 7.71. Found C, 55.72; H, 6.50; N, 7.95.

Preparation 8

(3R)-6-Cyclohexyl-3-[3-({[(4-fluorophenyl)sulfonyl]amino}carbonyl)-1,2,4-oxadiazol-5-yl]hexanoic acid

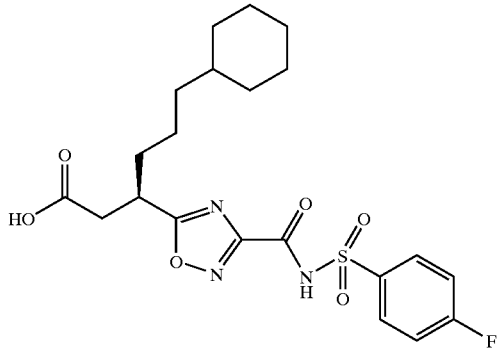

The title compound was obtained as a white foam from the title compound from Preparation 7, using a similar method to that described in Preparation 2, apart from the reaction was carried out in toluene.

$^1$H NMR (400 MHz, D$_6$-DMSO) □0.73–0.87 (m, 2H), 1.03–1.24 (m, 8H), 1.53–1.69 (m, 7H), 2.67–2.80 (m, 2H), 3.37–3.46 (m, 1H), 7.35 (m, 2H), 7.99 (m, 2H).

LRMS (ES) 466 (M−H).

Anal. Calcd. For C$_{21}$H$_{28}$FN$_3$O$_6$S+0.05 PhMe: C, 54.32; H, 5.64; N, 8.90. Found C, 53.95; H, 6.03; N, 8.54.

Preparation 9 tert-Buy (3R)-6-cyclohexyl-3[3-({[(4-isopropylphenyl)sulfonyl]amino}carbonyl)-1,2,4-oxadiazol-5-yl]hexanoate

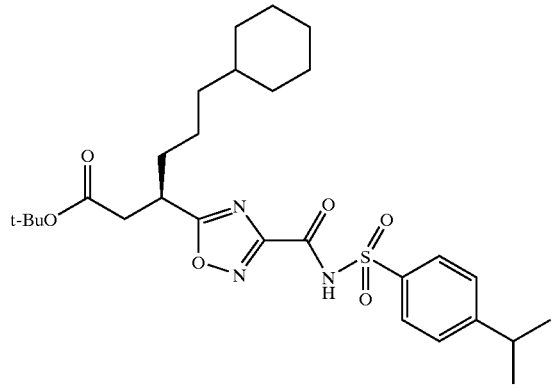

The title compound was obtained as a white foam from the title compound from Preparation 28 and 4-isopropylbenzenesulfonyl chloride, using a similar method to that described in Preparation 1.

$^1$H NMR (400 MHz, D$_6$-DMSO) □0.72–0.87 (m, 2H), 1.03–1.28 (m, 8H), 1.21 (d, 6H), 1.27 (s, 9H), 1.51–1.68 (m, 7H), 2.68–2.73 (m, 2H), 2.92–3.04 (m, 1H), 3.38–3.47 (m, 1H), 7.48 (d, 2H), 0.89 (d, 2H).

Anal. Calcd. For C$_{28}$H$_{41}$N$_3$O$_8$S+0.02 CH$_2$Cl$_2$: C, 61.26; H, 7.53; N, 7.65. Found C, 60.86; H, 7.64; N, 7.69.

Preparation 10

(3R)-6-Cyclohexyl-3-[3-({[(4-isopropylphenyl)sulfonyl]amino}carbonyl)-1,2,4-oxadiazol-5-yl]hexanoic acid

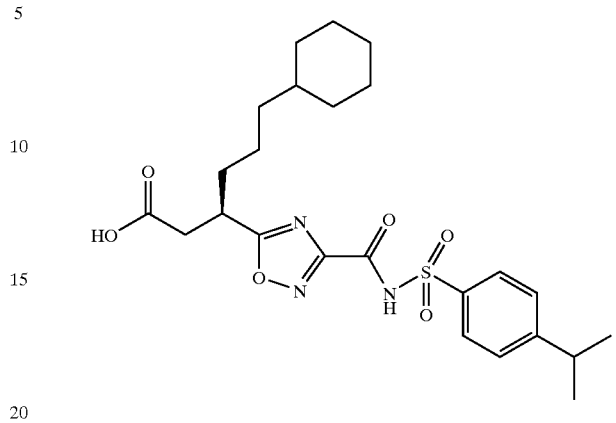

The title compound was obtained as a white foam from the title compound from Preparation 9, using a similar method to that described in Preparation 2, apart from the final product was azeotroped with diisopropyl ether.

$^1$H NMR (400 MHz, D$_6$DMSO) □0.72–0.86 (m, 2H), 1.03–1.27 (m, 8H), 1.24 (d, 6H), 1.51–1.70 (m, 7H), 2.67–2.80 (m, 2H), 2.95–3.03 (m, 1H), 3.41–3.48 (m, 1H), 7.48 (d, 2H), 7.90 (d, 2H).

LRMS (ES) 490 (M−H).

Anal. Calcd. For C$_{24}$H$_{33}$N$_3$O$_6$S+0.2 DIPE: C, 59.11; H, 7.05; N, 8.21. Found C, 58.93; H, 7.15; N. 8.14.

Preparation 11 tert-Butyl (3R)-6-cyclohexyl-3-[3-({[(3,4-dimethoxyphenyl)sulfonyl]amino}carbonyl)-1,2,4-oxadiazol-5-yl]hexanoato

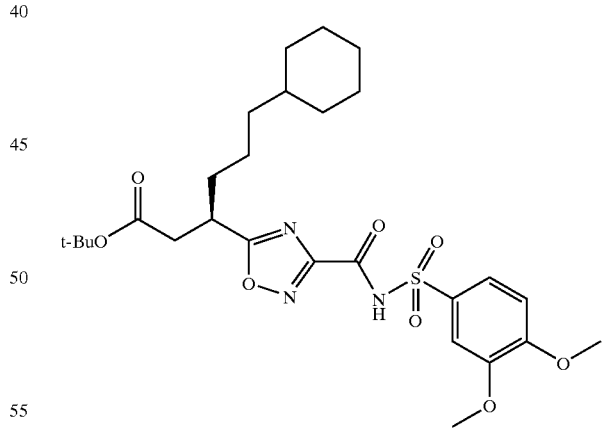

The title compound was obtained as a clear oil from the title compound from Preparation 28 and 3,4-dimethoxylbenzenesulfonyl chloride, using a similar method to that described in Preparation 1.

$^1$H NMR (400 MHz, D$_6$-DMSO) □0.71–0.84 (m, 2H), 1.03–1.28 (m, 8H), 1.30 (s, 9H), 1.52–1.67 (m, 7H), 2.632.77 (m, 2H), 3.30–3.39 (m, 1H), 3.76 (s, 3H), 3.79 (s, 3H), 7.02 (d, 1H), 7.40–7.47 (m, 2H).

LRMS (ES) 564 (M−H).

Preparation 12

(3R)-6-Cyclohexyl-3-[3-({[(3,4-dimethoxyphenyl)sulfonyl]amino}carbonyl)-1,2,4-oxadiazol-5-yl]hexanoic acid

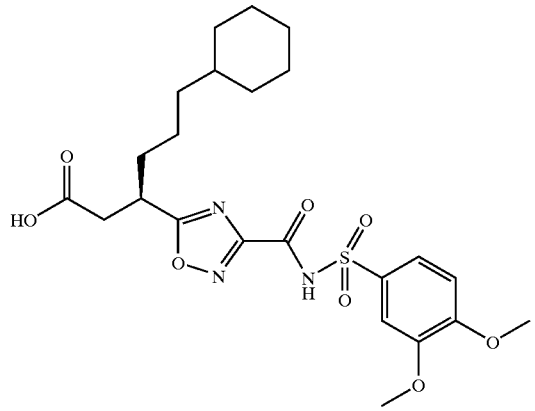

The title compound was obtained as a white foam from the title compound from Preparation 11, using a similar method to that described in Preparation 2.

$^1$H NMR (400 MHz, $D_6$—DMSO) □0.73–0.88 (m, 2H), 1.08–1.24 (m, 8H), 1.55–1.70 (m, 7H), 2.66–2.80 (m, 2H), 3.37–3.46 (m, 1H), 3.79 (s, 3H), 3.82 (s, 3H), 7.08 (d, 1H), 7.44 (s, 1H), 7.52 (d, 1H).

LRMS (ES) 508 (M−H).

Preparation 13 tert-Butyl (3R)-6-cyclohexyl-3-(3-{[(8-quinolinylsulfonyl)amino]carbonyl}-1,2,4-oxadiazol-5-yl)hexanoate

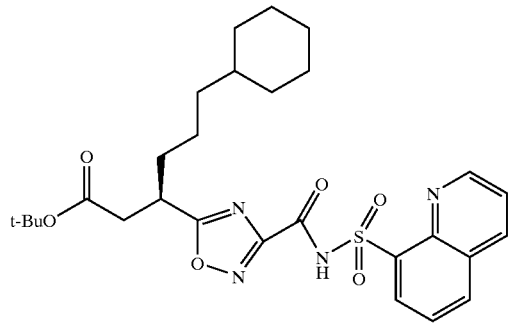

The title compound was obtained as a white solid from the title compound from Preparation 28 and 8-quinolinesulfonyl chloride, using a similar method to that described in Preparation 1.

Mpt 107–109° C.

$^1$H NMR (400 MHz, $D_6$-DMSO) □0.70–0.84 (m, 2H), 1.02–1.30 (m, 17H), 1.50–1.67 (m, 7H), 2.63–2.70 (m, 2H), 3.31–3.42 (m, 1H), 7.76 (dd, 1H), 7.84 (dd, 1H), 8.38 (d, 1H), 8.51 (d, 1H), 8.66 (d, 1H), 9.07 (d, 1H).

LRMS (ES) 555 (M−H).

Anal. Calcd. For $C_{28}H_{36}N_4O_6S$: C, 60.41; H, 6.52; N, 10.06. Found C, 60.01; H. 6.52; N, 9.98.

Preparation 14

(3R)-6-Cyclohexyl-3-(3-{[(8-quinolinylsulfonyl)amino]carbonyl}-1,2,4-oxadiazol-5-yl)hexanoic acid

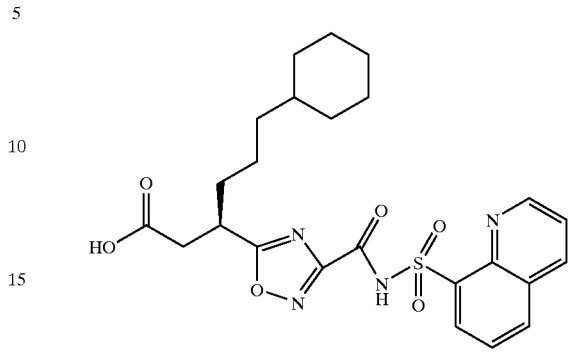

The title compound was obtained as a white solid from the title compound from Preparation 13 using a similar method to that described in Preparation 2.

Mpt 68–72° C.

$^1$H NMR (400 MHz, $D_6$-DMSO) p0.70–0.84 (m, 2H), 1.00–1.22 (m, 8H), 1.50–1.67 (m, 7H), 2.65–2.79 (m, 2H), 3.37–3.45 (m, 1H), 7.78 (dd, 1H), 7.87 (dd, 1H), 8.40 (d, 1H), 8.52 (d, 1H), 8.68 (d, 1H), 9.10 (d, 1H).

LRMS (ES) 499 (M−H).

Preparation 15 tert-Butyl (3R)-6-cyclohexyl-3-[3-({[(3,5-dimethyl-4-isoxazolyl)sulfonyl]amino}carbonyl)-1,2,4-oxadiazol-5-yl]hexanoate

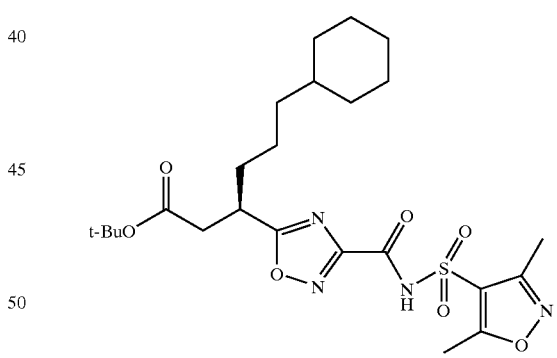

The title compound was obtained as a clear oil from the title compound from Preparation 28 and 3,5-dimethyl-4-isoxazolesulfonyl chloride, using a similar method to that described in Preparation 1.

$^1$H NMR (400 MHz, $D_6$-DMSO) □0.74–0.85 (m, 2H), 1.03–1.30 (m, 17H), 1.53–1.67 (m, 7H), 2.30 (s, 3H), 2.58 (s, 3H), 2.66–2.74 (m, 2H), 3.34–3.45 (m, 1H).

LRMS (ES) 523 (M−H).

Anal. Calcd. For $C_{24}H_{36}N_4O_7S$: C, 54.95; H, 6.92; N, 10.68. Found C, 55.30H, 7.05; N, 10.55.

Preparation 16

(3R)-6-Cyclohexyl-3-[3-({[(3,5-dimethyl-4-isoxazolyl)sulfonyl]amino)carbonyl)-1,2,4-oxadiazol-5-yl]hexanoic acid

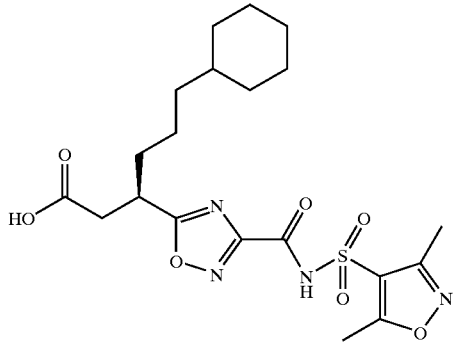

The title compound was obtained as a yellow foam from the title compound from Preparation 15, using a similar method to that described in Preparation 2, apart from the final product was azeotroped with diisopropyl ether.

$^1$H NMR (400 MHz, D$_6$-DMSO) □0.74–0.85 (m, 2H), 1.03–1.24 (m, 8H), 1.51–1.68 (m, 7H), 2.32 (s, 3H), 2.58 (s, 3H), 2.67–2.79 (m, 2H), 3.38–3.45 (m, 1H).

Anal. Calcd. For $C_{20}H_{28}N_4O_7S+0.12$ DIPE: C, 51.76; H, 6.22; N, 11.65. Found C, 51.66; H, 6.44; N, 11.27.

Preparation 17 tert-Butyl (3R)-6-cyclohexyl-3-(3-{[(isopropylsulfonyl)amino]carbonyl}-1,2,4-oxadiazol-5-yl)hexanoate

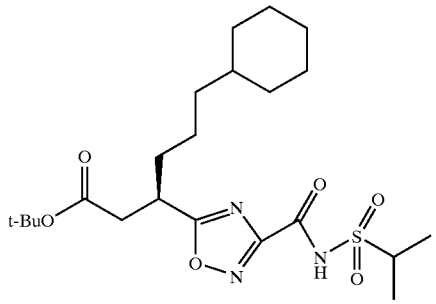

The title compound was obtained as a clear glass from the title compound from Preparation 28 and 2-propanesulfonyl chloride, using a similar method to that described in Preparation 1.

$^1$H NMR (400 MHz, CDCl$_3$) □0.75–0.92 (m, 2H), 1.06–1.90 (m, 30H), 2.62–2.88 (m, 2H), 3.08–3.24 (m, 1H), 3.57–3.68 (m, 1H).

LRMS (ES) 470 (M−H).

Anal. Calcd. For $C_{22}H_{37}N_3O_6S+1.29H_2O$: C, 53.40; H, 8.06; N, 8.49. Found C, 53.46; H, 7.41; N, 8.41.

Preparation 18

(3R)-6-Cyclohexyl-3-(3-{[(isopropylsulfonyl)amino]carbonyl}-1,2,4-oxadiazol-5-yl)hexanoic acid

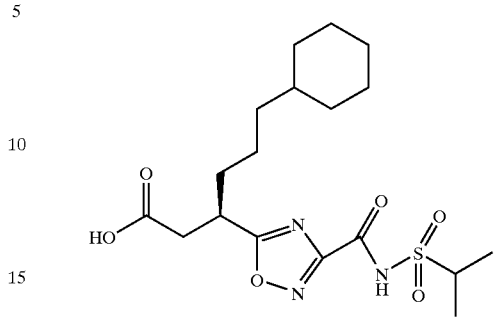

The title compound was obtained as a yellow foam from the title compound from Preparation 17, using a similar method to that described in Preparation 2, apart from the reaction was carried out in neat trifluoroacetic acid.

$^1$H NMR (400 MHz, CDCl$_3$) □0.77–0.98 (m, 2H), 1.04–1.95 (m, 21H), 2.73–3.04 (m, 2H), 3.50–3.68 (m, 1H), 3.78–3.95 (m, 1H).

LRMS (ES) 414 (M−H).

Anal. Calcd. For $C_{18}H_{29}N_3O_6S+0.9$ TFA: C, 45.90; H, 5.82; N, 8.11. Found C, 45.96; H, 6.06; N, 8.34.

Preparation 19 tert-Butyl(3R)-6-cyclohexyl-3-(3-{[methyl(methylsulfonyl)amino]carbonyl}-1,2,4-oxadiazol-5-yl)hexanoate

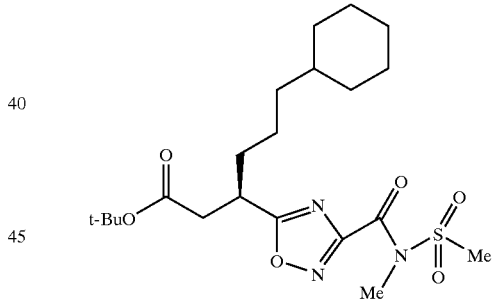

To a solution of the tide compound from Preparation 29 (0.50 g, 1.3 mmol) in tetrahydrofuran (10 mL) at −78° C. was added lithium bis(trimethylsilyl)amide (1.4 mL of a 1.0 mol L$^{-1}$ solution in tetrahydrofuran, 1.4 mmol). The reaction was stirred for 45 minutes then methanesulfonyl chloride (0.11 mL, 1.4 mmol) was added. The reaction was warmed to room temperature after 5 hours and then stirred overnight. The mixture was quenched with water (10 mL) and then extracted with ethyl acetate (2×20 mL). The combined organic extracts were dried (Na$_2$SO$_4$) and the solvents removed in vacuo. The residue was purified by flash chromatography on silica gel (elution with pentane/ethyl acetate 80:20) to give the title compound as a clear oil (0.42 g).

$^1$H NMR (400 MHz, CDCl$_3$) □0.77–0.93 (m, 2H), 1.07–1.48 (m, 17H), 1.58–1.82 (m, 7H), 2.63 (dd, 1H), 2.81 (dd, 1H), 3.32–3.59 (m, 7H).

LRMS (ES) 480 (M+Na).

Preparation 20

(3R)-6-Cyclohexyl-3(3-{[methyl(methylsulfonyl)amino]carbonyl}-1,2,4-oxadiazol-5-yl)hexanoic acid

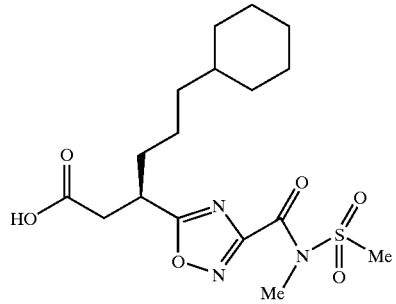

The title compound was obtained as a yellow oil from the title compound from Preparation 19, using a similar method to that described in Preparation 2, apart from the reaction was carried out in neat trifluoroacetic acid.

$^1$H NMR (400 MHz, CDCl$_3$) □00.78–0.94 (m, 2H), 1.05–1.39 (m, 8 H), 1.58–1.87 (m, 7H), 2.80 (dd, 1H), 2.98 (dd, 1H), 3.34 (s, 3H), 3.40 (s, 3H), 3.59 (m, 1H).

LRMS (ES) 400 (M–H).

Anal. Calcd. For C$_{17}$H$_{27}$N$_3$O$_6$S: C, 50.86; H, 6.78; N, 10.47. Found C, 50.72; H, 6.83; N, 10.34.

Preparation 21 tert-Butyl (3R)-6-cyclohexyl-3-[3-({[(phenylmethyl)sulfonyl]amino}carbonyl)-1,2,4-oxadiazol-5-yl]hexanoate

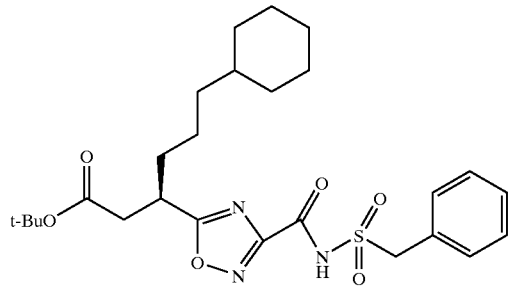

The title compound was obtained as a white foam from the title compound from Preparation 28 and phenylmethanesulfonyl chloride, using a similar method to that described in Preparation 1.

$^1$H NMR (400 MHz, CDCl$_3$) □0.78–0.92 (m, 2H), 1.07–1.81 (m, 24H), 2.52–2.84 (m, 2H), 3.47 (m, 1H), 4.78 (s, 2H), 7.10–7.44 (m, 5H).

LRMS (ES) 518 (M–H).

Anal. Calcd. For C$_{26}$H$_{37}$N$_3$O$_6$S+0.79H$_2$O: C, 58.49; H, 7.28; N, 7.87. Found C, 58.48; H. 6.97; N, 7.78.

Preparation 22

(3R)-6-Cyclohexyl-3-[3-({[(phenylmethyl)sulfonyl]amino}carbonyl)-1,2,4-oxadiazol-5-yl]hexanoic acid

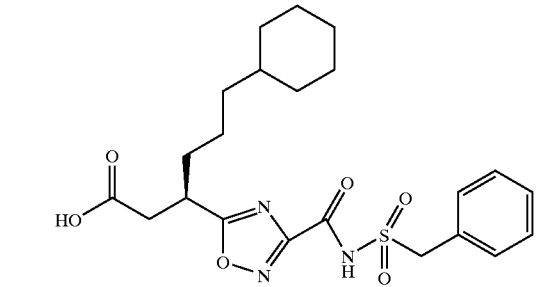

The title compound was obtained as a yellow foam from the title compound from Preparation 21, using a similar method to that described in Preparation 2, apart from the reaction was carried out in neat trifluoroacetic acid.

$^1$H NMR (400 MHz, CDCl$_3$) □0.88–0.97 (m, 2H), 1.05–1.42 (m, 8H), 1.57–1.88 (m, 7H), 2.72–3.01 (m, 2H), 3.53 (m, 1 H), 4.64–4.81 (m, 2H), 7.18–7.43 (m, 5H).

LRMS (ES) 462 (M–H).

Anal. Calcd. For C$_{22}$H$_{29}$N$_3$O$_8$S+0.86 TFA: C, 50.73; H, 5.36; N, 7.48. Found C, 50.38; H, 5.69; N, 7.67.

Preparation 23 tert-Butyl (3R)-6-cyclohexyl-3-{3-[(3-pyridyisulfonyl)amino]carbonyl)-1,2,4-oxadiazol-5-yl)hexanoate

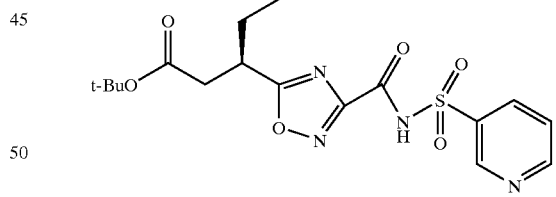

The title compound was obtained as a clear solid from the title compound from Preparation 28 and 3-pyridinesulfonyl chloride, using a similar method to that described in Preparation 3.

$^1$H NMR (400 MHz, CDCl$_3$) □0.78–0.94 (m, 2H), 0.99–1.77 (m, 24H), 2.58–2.84 (m, 2H), 3.57 (m, 1H), 7.29 (m, 1H), 8.25 (m, 1H), 8.64 (m, 1H), 9.12 (m, 1H).

LRMS (ES) 505 (M–H).

Anal. Calcd. For C$_{24}$H$_{34}$N$_4$O$_6$S+0.43 CH$_2$Cl$_2$: C, 54.02; H, 6.47; N, 10.32. Found C, 53.99; H, 6.33; N, 10.41.

Preparation 24
(3R)-6-Cyclohexyl-3(3-[(3-pyridylsulfonyl)amino]carbonyl}-1,2,4-oxadiazol-5-yl)hexanoic acid

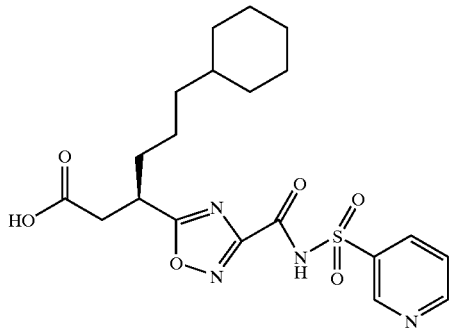

The title compound was obtained as a while solid from the title compound from Preparation 23 using a similar method to that described in Preparation 2, apart from the reaction was carried out in neat trifluoroacetic acid.

$^1$H NMR (400 MHz, CD$_3$OD) ⊓0.88–0.92 (m, 2H), 1.04–1.32 (m, 8H), 1.56–1.79 (m, 7H), 2.77 (dd, 1H), 2.86 (dd, 1H), 3.51 (m, 1H), 7.62 (m, 1H), 8.46 (d, 1H), 8.79 (d, 1H), 9.19 (S, 1H).

LRMS (ES) 224 [(M−2H)/2].

Anal. Calcd. For C$_{20}$H$_{26}$N$_4$O$_6$S+1.45 TFA: C, 44.68; H, 4.49; N, 9.10. Found C, 44.67; H, 4.60; N, 9.31.

Preparation 25: (2R)-2-[2-(tert-Butoxy)-2-oxoethyl]-5-cyclohexylpentanoic acid Route A:
(2R)-2[2-(tert-butoxy)-2-oxoethyl]-5-cyclohexylpentanoic acid

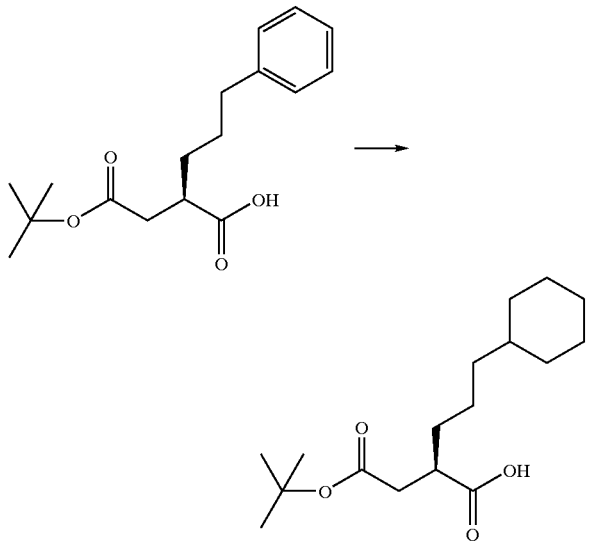

A solution of (2R)-2-[2-(tert-butoxy)-2-oxoethyl]-5-phenylpentanoic acid (Syn. Lett.; 1998; 637–639) (10.00 g, 34.2 mmol) in acetic acid (120 m)) was treated with 5% Rhodium on alumina catalyst, pressurised to 60 psi with hydrogen in a seated vessel and stirred at room temperature for 17 hours. The mixture was filtered through a pad of Arbocel® and the solvent was removed from the filtrate under reduced pressure. The residue was azeotroped from toluene to afford the title compound (7.53 g).

MS:299 (MH$^+$)

$^1$H-NMR (CDCl$_3$) δ: 2.80 (1H, m), 2.61 (1H, m), 2.38 (1H, m), 1.75–1.56 (7H, m), 1.55–1.04 (17H, m), 0.84 (2H, m).

Route B:
(4S)-4-Benzyl-3-(5-cyclohexylpentanoyl)-1,3-oxazolidin-2-one

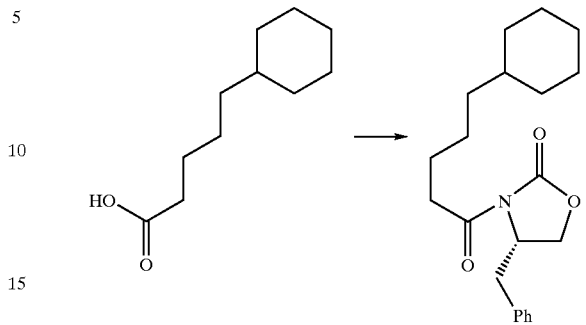

A solution of 5-cyclohexylpentanoic acid (63.50 g, 345 mmol) in N,N-dimethylformamide (0.5 ml) and dichloromethane (350 ml) was cooled to 5° C. and treated dropwise with oxalyl chloride (31.6 ml, 362 mmol) over 30 minutes. The mixture was stirred at 0° C. for 3 hours then the solvent was removed under reduced pressure to afford 5-cyclohexylpentanoyl chloride as a pale yellow solid (70.0 g).

A solution of n-butyllithium (100 ml, 250 mmol, 2.5M in hexanes) was added via a cannula to a solution of (4S)-4-benzyl-1,3-oxazolidin-2-one (44.30 g, 250 mmol) in anhydrous tetrahydrofuran (400 ml) at −78° C. The yellow solution was then stirred for 45 minutes. A solution of 5-cyclohexylpentanoyl chloride (55.5 g, 275 mmol) in tetrahydrofuran (100 ml) was then added over 1 hour. The mixture was stirred at −78° C. for 30 minutes then warmed to room temperature over 1 hour. The mixture was quenched with an aqueous solution of ammonium chloride (20% w/v, 400 ml) and extracted with ethyl acetate. The layers were separated and the organic layer was washed with brine, dried over anhydrous sodium sulphate and the solvent removed under reduced pressure. The solid was recrystallised from hexane (500 ml) to afford the title compound as a white solid (81.0 g).

MS: 344 (MH$^+$)

$^1$H-NMR (CDCl$_3$) δ: 7.41–7.13 (5H, m), 4.68 (1H, m), 4.27–4.02 (2H, m), 3.31 (1H, dd, J=16, 4 Hz), 3.06–2.70 (3H, m), 1.81–1.53 (7H, m), 1.49–1.04 (8H, m), 0.88 (2H, m)

tert-Butyl 3-{[(4S)-4-benzyl-2-oxo-1,3-oxazolidin-3-yl]carbonyl}-6-cyclohexylhexanoate

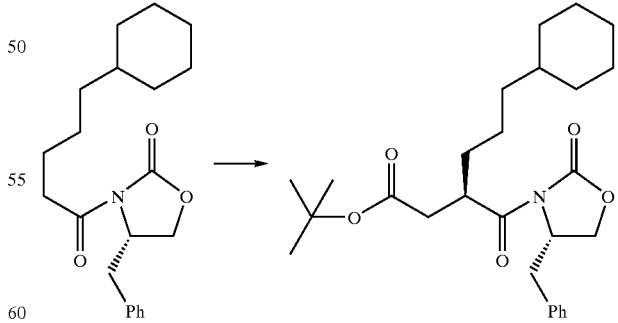

A solution of (4S)-4-benzyl-3-(5-cyclohexylpentanoyl)-1,3-oxazolidin-2-one (70.0 g, 204 mmol) in anhydrous tetrahydrofuran (650 ml) was cooled to −70° C. and treated dropwise with sodium hexamethyldisilazide (1M In tetrahydrofuran, 224 ml, 224 mmol) over 45 minutes. The mixture was stirred for a further 45 minutes before being treated with t-butylbromoacetate (31.6 ml, 214 mmol). This mixture was stirred at −70° C. for 30 minutes then warmed to −30° C. and quenched with an aqueous solution of ammonium chloride (20% w/v, 400 ml) and warmed to room temperature. The mixture was extracted with ethyl acetate and the combined organic extracts were washed with brine, dried over anhydrous sodium sulphate and the solvent removed under reduced pressure. The solid was recrystallised from hexane to afford the title compound as a white solid (71.4 g).

MS: 458(MH$^+$)

$^1$H-NMR (CDCl$_3$) δ: 7.41–7.13 (5H, m), 4.66 (1H, m), 4.23–4.03 (3H, m), 3.35 (1H, dd, J=16, 4 Hz), 2.95–2.68 (3H, m), 2.47 (1H, m), 1.80–1.07 (24H, m), 0.85 (2H, m)

2-[2-(tert-Butoxy)-2-oxoethyl]-5-cyclohexylpentanoic acid

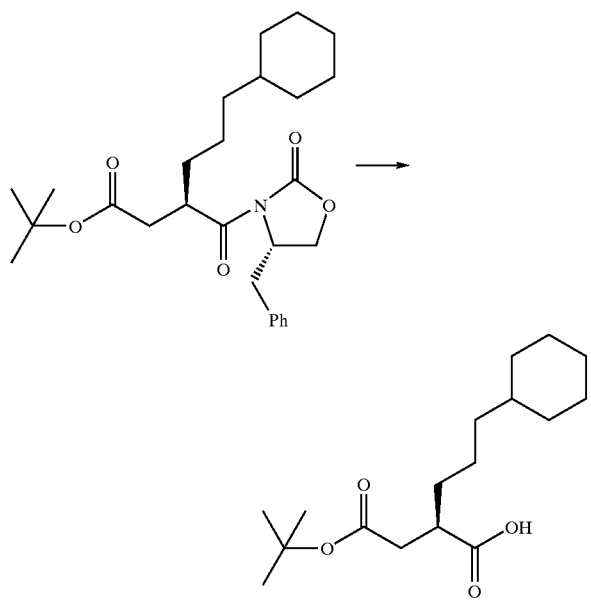

A solution of tert-butyl 3-([[(4S)-4-benzyl-2-oxo-1,3-oxazolidin-3-yl]carbonyl}-6-cyclohexylhexanoate (64.0 g, 139.9 mmol) in tetrahydrofuran: water (3:1, 800 ml) was cooled to 5,C then treated sequentially with hydrogen peroxide (30% w/v water, 87 m), 769 mmol) then lithium hydroxide hydrate (10.09, 238 mmol). The reaction was stirred for 1 hour then quenched by dropwise addition of an aqueous solution of sodium thiosulphate (500 ml) keeping the temperature below 20° C. The mixture was extracted with ethyl acetate (discarded) and the aqueous phase was acidified to pH 2 with solid citric acid and extracted with ethyl acetate. The combined organic phases were washed with brine, dried over anhydrous sodium sulphate and the solvent removed under reduced pressure. The residue was purified by column chromatography on silica gel eluting with a gradient system of hexane:ethyl acetate (2:1) gradually changing to hexane:ethyl acetate (1:1) to afford the title compound (40.7 g)

Route C:
3-(Diethoxyphosphoryl)succinic acid 1-tert-butyl ester

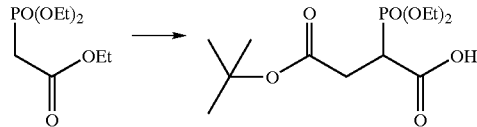

Triethylphosphonoacetate (102 g, 0.45 mol) was added dropwise over 11 min to a stirred solution of potassium tert-butoxide (60 g, 0.54 mol) in THF (500 ml), at 0° C., under nitrogen. The mixture was stirred for 1 hour at 0° C. and then dichloromethane (300 ml) was added and the reaction mixture was warmed to 25–30° C. The mixture was stirred at 25–30° C. for 1 hour and then added dropwise over 33 minutes to a solution of tert-butyl bromoacetate (96 g, 0.49 mol) in THF (500 ml), at 0° C., under nitrogen. The mixture was stirred at 0–5° C. for 2 hours and then a solution of citric acid (174 g, 0.91 mol) In demineralised water (250 ml) was added. The mixture was concentrated in vacuo to remove most of the THF and then toluene (750 ml) was added. The organic phase was separated, washed with brine (2×150 ml) and concentrated in vacuo to leave a colourless oil. The oil was taken up in ethanol and a solution of potassium hydroxide (36.g, 0.64 mol). In demineralised water (150 ml) was added dropwise over 15 mins. The mixture was stirred at 0° C. for 4 hours and then a solution of citric acid (158 g, 0.82 mol) in demineralised water (600 ml), and toluene (600 ml), were added. The organic phase was separated and the aqueous phase was re-extracted with toluene (600 ml). The combined organic phases were washed with demineralised water (2×150 ml) and concentrated in vacuo to leave a white solid. Toluene (150 ml) was added and the slurry was re-concentrated in vacuo to leave a white solid. The product was purified by crystallisation from tert-butylmethyl ether (300 ml) and cyclohexane (600 ml) to give the title compound as a solid (79 g).

$^1$H-NMR (CDCl$_3$) δ: 4.20–4.10 (4H, m), 3.49–3.36 (1H, m), 3.00–2.85 (1H, m), 2.72–2.60 (1H, m), 1.20 (9H, s), 1.37–1.27 (6H, m)

Alternative preparation:

Triethylphosphonoacetate (12.0 Kg, 53.5 mol) was added over 30 minutes to a stirred solution of potassium tert-butoxide (7.20 Kg, 64.2 mol) in THF (118 litres), between 0 and 5° C., under nitrogen. The mixture was warmed to 25–30° C. where it was stirred for 1 hour and then added over 45 minutes to a solution of tert-butyl bromoacetate (11.5 Kg, 59.0 mol) in THF (28 litres), between 0 and 5° C., under nitrogen. The mixture was stirred at 0–5° C. for 1 hour and then demineralised water (6.1 litres) and ethanol (30 litres) were added. A solution of potassium hydroxide (4.2 Kg, 75.0 mol) in demineralised water (84 litres) was then added over 2 hours, between −5 and 0° C. The mixture was stirred at −10° C. for 16 hours and then a solution of citric acid (16.5 Kg, 85.8 mol) In demineralised water (32 litres) was added. The mixture was concentrated in vacuo to a volume of 180 litres and then ethyl acetate (90 litres) was added. The organic phase was separated and the aqueous phase was re-extracted with ethyl acetate (30 litres). The combined organic phases were washed with water (30 litres) and then stripped and replaced with cyclohexane by distillation at atmospheric pressure, at a constant volume of 72 litres. tert-Butylmethyl ether (18 litres) was added and the mixture was stirred at ambient temperature for 12 hours and then filtered. The residue was washed with a mixture of cyclohexane (16 litres) and tert-butylmethyl ether (3.6 litres) then dried in vacuo for 16 rs to give the title compound as a colourless solid (10.0 Kg, 60%).

$^1$H-NMR (CDCl$_3$) δ: 4.20–4.10 (4H, m), 3.49–3.36 (1H, m), 3.00–2.85 (1H, m), 2.72–2.60 (1H, 1.20 (9H, s), 1.37–1.27 (6H, m)

(E)-2-[2-(tert-Butoxy)-2-oxoethyl]-5-phenyl-2-pentenoic acid

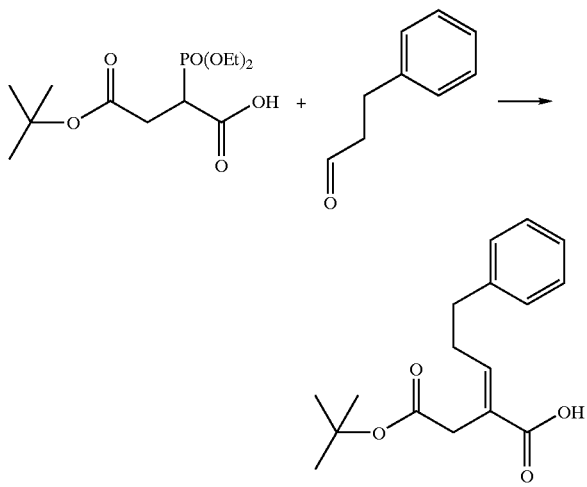

A solution of 3-(diethoxyphosphoryl)succinic add 1-tert-butyl ester (100 g, 0.32 mol) in THF 300 ml) was added dropwise over 15 min to a stirred solution of potassium tert-butoxide (110 g, 0.98 mol) in THF (300 ml), between −10 and −5° C., under nitrogen. The mixture was stirred at −10° C. for 15 min and then a solution of hydrocinnamaldehyde (46.8 g, 0.35 mmol) in THF (100 ml) was added dropwise over 15 min, between −13 and −8° C. The mixture was stirred at −10° C. for 30 min and then a solution of citric acid (111 g, 0.58 mol) in demineralised water (500 ml), and ethyl acetate (500 ml), were added. The pH was adjusted to pH 4 with aqueous sodium hydroxide solution (50%) and the phases were separated. The aqueous fraction was washed with ethyl acetate (500 ml) and the combined organic fractions were washed with saturated sodium bicarbonate solution (500 ml), citric acid solution (10%, 500 ml) and demineralised water (500 ml) and then concentrated in vacuo. The resulting solid was slurried in cyclohexane (470 ml) for 1 hour and then the mixture was filtered. The residue was washed with cyclohexane (2×50 ml) and dried in vacuo to leave the title compound as a colourless solid (76 g, 81%).

MS:289 [(M−H)].

$^1$H-NMR (CDCl$_3$) δ: 7.33–7.16 (5H, m), 7.05 (1H, br t), 3.20 (2H, s), 2.89 (2H, br t), 2.50 (2H, br dd), 1.41 (9H, s)

(R)-2-[2-(tert-Butoxy)-2-oxoethyl]-5-phenylpentanoic acid

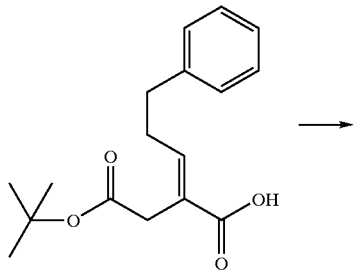

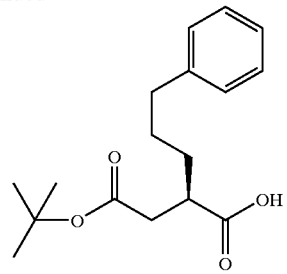

A stirred solution of (E)-2-[2-(tert-butoxy)-2-oxoethyl]-5-phenyl-2-pentenoic acid (100 g, 0.34 mol), cyclohexylamine (39 ml, 0.34 mol) and [(S)-2,2'-bis(diphenylphosphino-1,1'-binaphthyl]chloro(p-cymene) ruthenium chloride (0.64 g, 0.69 mmol) in methanol (1000 ml) was heated to 60° C., under hydrogen (60 p.s.i.), for 42 hours and then allowed to cool to room temperature. The mixture was filtered through celite and then concentrated in vacuo to a yellow solid which was purified by re-crystallisation from acetone (850 ml). The resulting solid was partitioned between ethyl acetate (1200 ml) and citric acid solution (10%, 1200 ml) and the organic phase was separated, washed with demineralised water (1200 ml) and concentrated in vacuo to leave the title compound as an oil (80 g).

$^1$H-NMR (CDCl$_3$) δ: 7.30–7.17 (5H, m), 2.85–2.78(1H, m), 2.66–2.58 (3H, m), 2.37 (1H, br dd), 1.75–1.51 (4H, m), 1.40 (9H, s)

Preparation of cyclohexylamine salt:

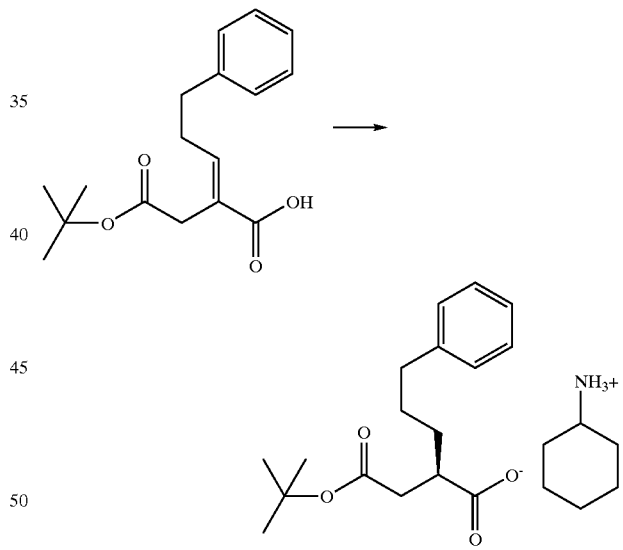

A stirred solution of cyclohexylamine (266 ml, 2.32 mol), (E)-2-[2-(tert-butoxy)-2-oxoethyl]-5-phenyl-2-pentenoic acid (688 g, 2.37 mol and [(S)-2,2'-bis(diphenylphosphino-1,1'-binaphthyl]chloro(p-cymene)ruthenium chloride (4.4 g, 4.7 mmol) in methanol (6.9 litres) was heated to 60° C., under hydrogen (60 p.s.i.), for 47 hours and then allowed to cool to room temperature (enantiomeric excess=88%). The mixture was filtered through celite and then the solvent was stripped and replaced with acetone by distillation at atmospheric pressure, at a constant volume of 4.2 litres. The resulting suspension was cooled to room temperature where it was stirred for 4 hours and then filtered. The residue was washed with acetone (2×1 litre) and then dried in vacuo at 45° C. for 16 hours to leave the title compound as a colourless solid (590 g, 64%, enantiomeric excess=98.9%).

¹H-NMR (CD₃OD) δ: 7.23–7.09 (5H, m), 3.05–2.98 (1H, m), 2.64–2.56 (3H, m), 2.53 (1H, dd, J 15.2, 7.2 Hz), 2.23 (1H, dd, J15.2, 7.2 Hz), 2.00–1.97, (2H, m), 1.85–1.81 (2H, m), 1.72–1.20 (10H, m), 1.40 (9H, s)

(R)-2-[2-(tert-Butoxy)-2-oxoethyl]-5-cyclohexylpentanoic acid cyclohexylamine salt

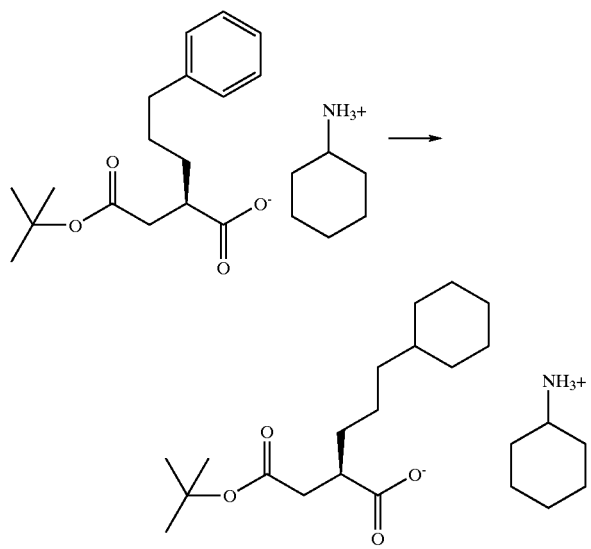

(R)-2-[2-(tert-Butoxy)-2-oxoethyl]-5-phenylpentanoic acid cyclohexylamine salt (6919, 1.77 mol) and ethyl acetate (7.0 litres) were added to an aqueous solution of citric acid (10%, 6.3 litres) and the organic phase was separated, washed with water (7.0 litres) and concentrated in vacuo to a yellow oil. A solution of the oil and 5% rhodium on carbon (51.6 g) in methanol (7.0 litres) was stirred at ambient temperature, under hydrogen (150 p.s.i.) for 48 hours and then filtered through celite. To the filtrate was added cyclohexylamine (202 ml, 1.77 mol) and the methanol solution was stripped and replaced with methylethyl ketone by distillation at atmospheric pressure, to a volume of 5.5 litres. The mixture was allowed to cool to ambient temperature where it was stirred for 48 hours and then filtered. The residue was washed with methylethyl ketone (2×500 ml) and then dried in vacuo at 45° C. for 4 hours to leave the title compound as a colourless solid (495 g, 71%).

¹H-NMR (CD₃OD) δ: 3.06–2.99 (1H, m), 2.63–2.56 (1H, m), 2.53 (1H, dd, J 15.2, 7.2 Hz), 2.23 (1H, dd, J 15.2, 7.2 Hz), 2.02–1.97 (2H, m), 1.77–1.15 (21H, m), 1.43 (9H, s), 0.93–0.82 (2H, m)

(R)-2-[2-(tert-Butoxy)-2-oxoethyl]-5-cyclohexylpentanoic acid

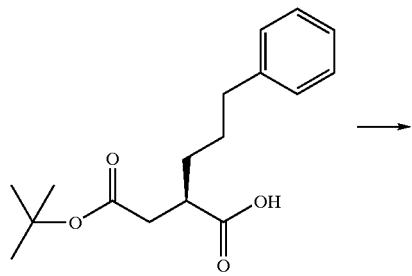

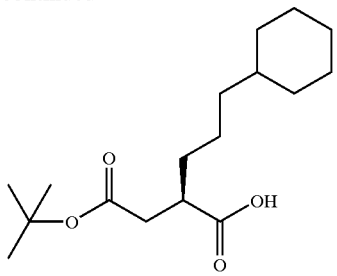

A solution of (R)-2-[2-(tert-butoxy)-2-oxoethyl]-5-phenylpentanoic acid (2.2 g, 7.5 mmol) and 5% Rh/C (0.22 g) in methanol (220 ml) was stirred at room temperature, under hydrogen 150 p.s.i.) for 24 hours and then filtered through celite. The filtrate was concentrated in vacuo to leave the title compound as an oil (2.0 g).

¹H-NMR (CDCl₃) δ: 2.82–2.76 (1H, m), 2.60 (1H, br dd), 2.37 (1H, br dd), 1.70–1.60 (6H, m), 1.51–1.30 (3H, m), 1.42 (9H, s), 1.23–1.11 (6H, m), 0.96–0.80 (2H, m)

Preparation 26:

tert-Butyl (3R)-3-[({[(Z)-1-amino-2-ethoxy-2-oxoethylidene]amino}oxy)carbonyl]-6-cyclohexylhexanoate

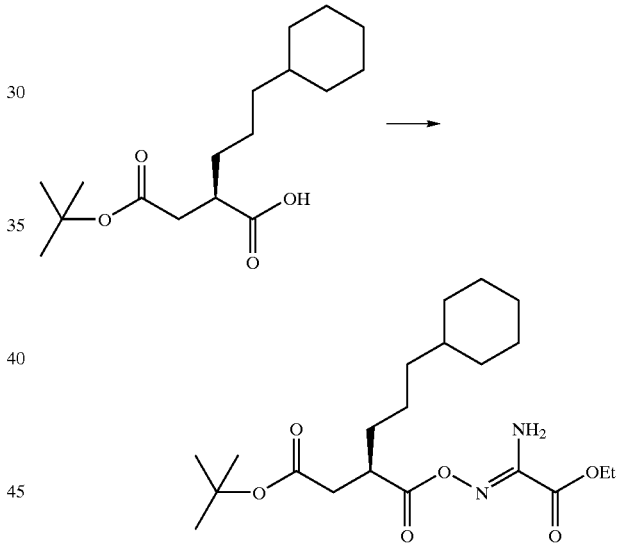

A solution of (2R)-2-[2-(tert-butoxy)-2-oxoethyl]-5-cyclohexylpentanoic acid (Preparation 25) (7.53 q, 25.2 mmol) in 1,4-dioxane (175 ml) was treated with 1-hydroxybenzotriazole hydrate (3.75 g, 27.8 mmol) and the mixture cooled to 0° C. N,N'-Dicyclohexylcarbodiimide (5.47 g, 26.5 mmol) was then added and the mixture was stirred for 3 hours being allowed to warm to room temperature over this time. The mixture was then filtered and washed with 1,4-dioxane (2×50 ml). The filtrate was then treated with sodium carbonate (4.01 g, 37.8 mmol) and ethyl 2-amino-2-(hydroxyimino)acetate (J. Org. Chem.;23; 1958; 1794) (3.339, 25.2 mmol). The resulting mixture was stirred at room temperature for 17 hours. The solvent was removed under reduced pressure and the residue was partitioned between ethyl acetate and water. The layers were separated and the aqueous phase was extracted with ethyl acetate (x). The combined organic layers were dried over anhydrous magnesium sulphate, filtered and the solvent removed under reduced pressure. The residue was purified by column chromatography on silica gel eluting with a gradient system of ethyl acetate: pentane (30: 70) gradually changing to ethyl acetate: pentane (50:50) to afford the title compound as a white solid (6.50 g).

MS: 413 (MH+)

$^1$H-NMR (CDCl$_3$) δ: 5.71 (2H, br s), 4.39 (2H, q), 2.92 (1H, m), 2.67 (1H, dd), 2.44 (1H, dd), 1.75–1.32 (22H, m), 1.26–1.04 (5H, m), 0.84 (2H, m).

Preparation 27

Ethyl 5-(1R)-1-[2-(tert-butoxy)-2-oxoethyl]-4-cyclohexylbutyl}1,2,4-oxadiazole-3-carboxylate

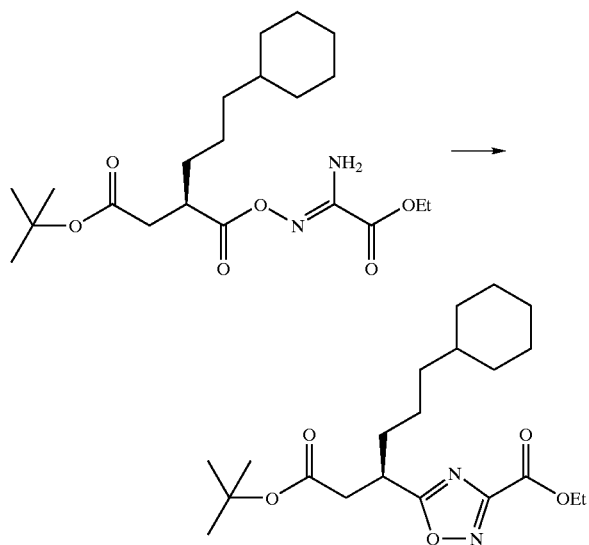

A solution of tert-Butyl (3 R)-3-[({[(Z)1-amino-2-ethoxy-2-oxoethylidene]amino}oxy)carbonyl]-6-cyclohexylhexanoate (Preparation 26)(21.0 g, 50.82 mmol) in xylene (400 ml) was heated at 130° C. for 17 hours, then allowed to cool to room temperature. The residue was purified by column chromatography on silica gel eluting with a gradient system of ethyl acetate:pentane (5:95) gradually changing to ethyl acetate:pentane (20:80) to afford the title compound as a colourless oil (20.0 g).

MS 395 (MH+), 412 (MNH$_4$+)

$^1$H-NMR (CDCl$_3$) δ: 4.51 (2H, m), 3.54 (1H, m), 2.86 (1H, dd), 2.65 (1H, dd), 1.86–1.57 (7H, m), 1.50–1.33 (12H, m), 1.30–1.03 (5H, m), 0.82 (2H, m).

Preparation 28 tert-Butyl (3R)-3-[3(aminocarbonyl)-1,2,4-oxadiazol-5-yl]-6-phenylhexanoate

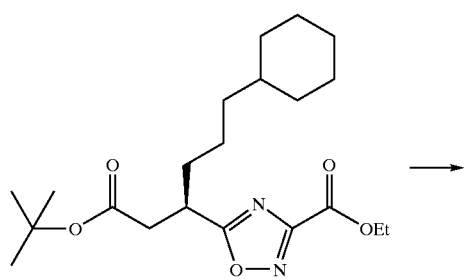

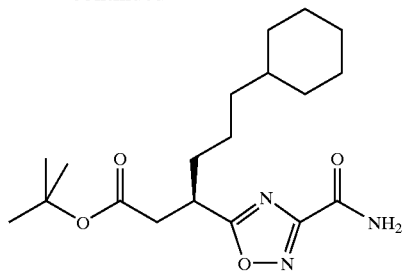

A solution of ethyl 5-{(1R)-1-[2-(tert-butoxy)-2-oxoethyl]-4-cyclohexylbutyl}-1,2,4-oxadiazole-3-carboxylate (Preparation 27) (400 mg, 1.01 mmol) in ethanol saturated with ammonia gas (20 ml) was stirred at room temperature for 18 hours. The solvent was removed under reduced pressure and the residue was purified by column chromatography on silica gel eluting with a gradient system of hexane:ethyl acetate (90:10) gradually changing to hexane:ethyl acetate (60:40) to afford the title compound as a white solid (260 mg).

MPt: 77–79° C.

MS: 366 (MH+), 383 (MNa+)

Analysis: Found C, 62.42; H, 8.59; N, 11.48%; C$_{19}$H$_{31}$N$_3$O$_4$ requires C, 62.44; H, 8.55; N, 11.50%

$^1$H-NMR (CDCl$_3$) δ:6.80 (1H, br s), 5.90 (1H, br s), 3.53 (1H, m), 2.87 (1H, dd, J=17, 9 Hz), 2.66 (1H, dd, J=17, 5 Hz), 1.90 1.50 (7H, m), 1.46–1.02 (17H, m), 0.83 (2H, m).

Preparation 29 tert-Butyl (3R)-6-cyclohexyl-3-{3-[(methylamino) carbonyl]-1,2,4-oxadiazol-5-yl}hexanoate

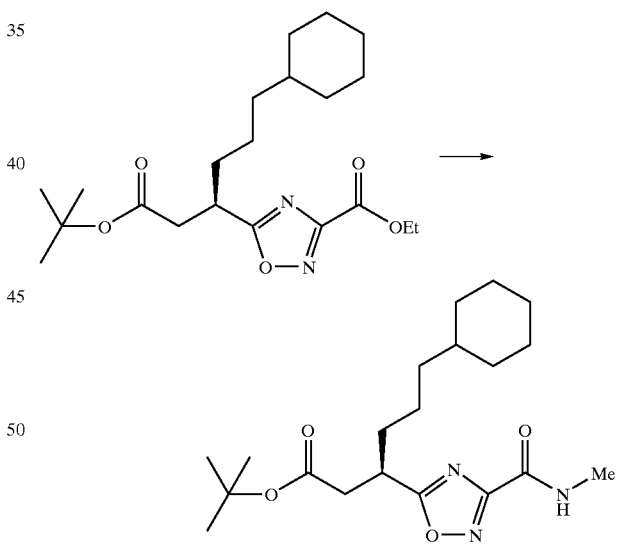

A solution of ethyl 5-{(1R)-1-[2-(tert-butoxy)-2-oxoethyl]4-cyclohexylbutyl}-1,2,4-oxadiazole-3 carboxylate (Preparation 27) (4.70 g, 11.9 mmol) In ethanol (80 ml) was treated with methylamine (33% w/v in ethanol, 12.0 ml, 96.0 mmol) and the solution was stirred at room temperature for 18 hours. The solvent was removed under reduced pressure and the residue was purified by column chromatography on silica gel eluting with a gradient system of dichloromethane:ethyl acetate (9:1) gradually changing to dichloromethane:ethyl acetate (8:2) to afford the title compound as a pale yellow oil which crystallised on standing (4.23 g).

MS: 380 (MH+)

¹H-NMR (CDCl₃) δ: 6.97 (1H, br m), 3.48 (1H, m), 3.04 (3H, d), 2.84 (1H, dd, J=17, 9 Hz), 2.66 (1H, dd, J-17, 4 Hz), 1.84–1.55 (7H, m), 1.39 (9H, s), 1.33.1.02 (8H, m), 0.83 (2H, m).

Preparation 30 tert-Butyl (3R)-6-cyclohexyl-3-({[(1S)-2-ethoxy-1-(hydroxymethyl)-2-oxoethyl]amino}carbonyl)hexanoate

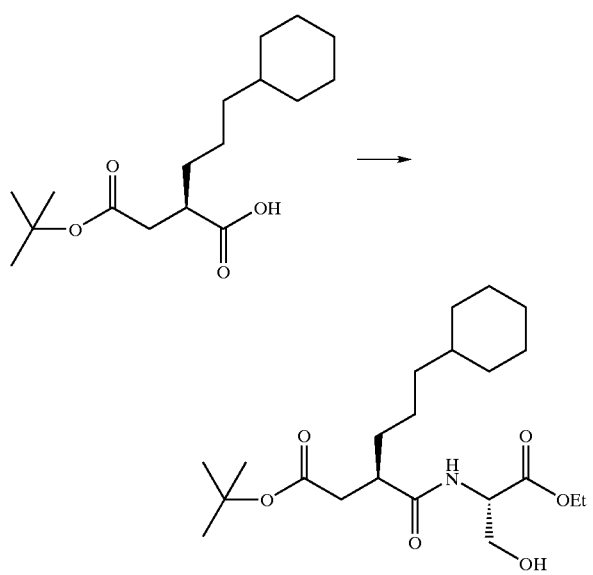

A solution of (2R)-2-[2-(tert-butoxy)-2-oxoethyl]-5-cyclohexylpentanoic acid (Preparation 25) (5.00 g, 16.76 mmol) in dichloromethane (75 ml) was treated sequentially with 1-hydroxybenzotriazole hydrate (2.49 g, 18.43 mmol), serine ethyl ester hydrochloride (3.13 g, 18.43 mmol) and N,N-diisopropylethylamine (6.13 ml, 35.19 mmol) and the resulting mixture was stirred at 0° C. under a nitrogen atmosphere for 15 minutes. 1-[3-(dimethylamino)propyl]-3-ethylcarbodiimide hydrochloride (3.53 g, 18.43 mmol) was then added and the mixture was stirred for 48 hours being allowed to warm to room temperature over this time, The mixture was diluted with dichloromethane (200 ml), washed sequentially with water, aqueous citric acid solution (10% w/v), a saturated aqueous solution of sodium hydrogen carbonate and brine, dried over anhydrous magnesium sulphate, filtered and the solvent removed under reduced pressure. The residue was then purified by column chromatography on silica gel eluting a gradient system of ethyl acetate: pentane (10:90) to (50:50) to afford the title compound as a colourless oil (5.41 g).

MS: 413 (M)

Analysis: Found C, 63.20: H, 9.52; N. 3.27%; C₂₂H₃₉NO₆. 0.33 EtOAc requires C, 63.28; H, 9.48; N, 3.16%

¹H-NMR (CDCl₃) δ: 6.50 (1H, br d, J=6 Hz), 4.60 (1H, m), 4.26 (2H, q, J=8 Hz), 4.09 (1H, m), 3.85 (1H, m), 3.18 (1H, m), 2.70 (1H, dd, J=18, 9 Hz), 2.51 (1H, m), 2.37 (1H, dd, J=18, 3 Hz), 1.78–1.52 (7H, m), 1.50–1.02 (20H, m), 0.85 (2H, m)

Preparation 31

Ethyl (4S)-2-{(1R)-1-[2-(tert-butoxy)-2-oxoethyl]-4-cyclohexylbutyl}-4,5-dihydro-,3-oxazole4-carboxylate

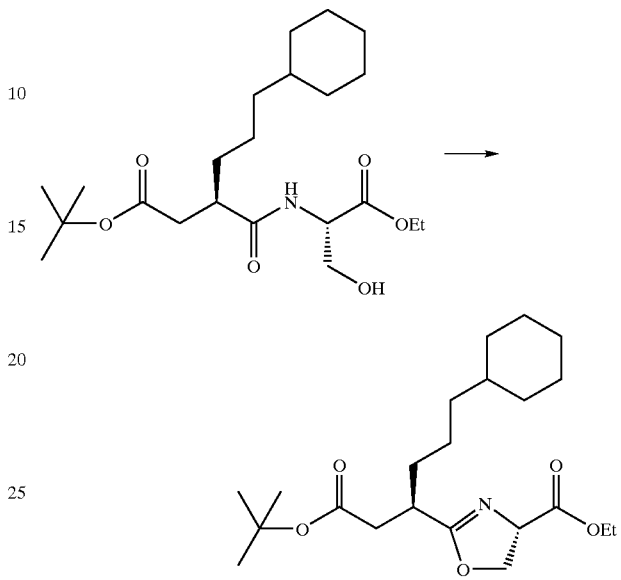

A solution of tert-butyl (3R)-6-cyclohexyl-3-({[(1S)-2-ethoxy-1-(hydroxymethyl)-2-oxoethyl]amino}carbonyl)hexanoate (Preparation 30) (4.14 g, 10 mmol) in anhydrous tetrahydrofuran (40 ml) was treated with (methoxycarbonylsulfamoyl)triethylammonium hydroxide, inner salt [Burgess Reagent] (2.62 g, 11 mmol) and the resulting mixture was heated under reflux under a nitrogen atmosphere for 1 hour. The solvent was removed under reduced pressure and the residue purified by column chromatography on silica gel eluting with a gradient system of pentane: ethyl acetate (80:20) to (50:50) to afford the title compound as a colourless oil (3.10 g)

¹H-NMR (CDCl₃) δ: 4.69 (1H, m), 4.52–4.33 (2H, m), 4.22 (2H, m), 2.87 (1H, m), 2.63 (1H, dd, J=16, 7 Hz), 2.40 (1H, dd, J=16, 6 Hz), 1.76–1.03 (27H, m), 0.85 (2H, m)

Preparation 32

Ethyl 2-{(1R)-1-[2-(tert-butoxy)-2-oxoethyl]-4-cyclohexylbutyl}-1,3-oxazole-4-carboxylate

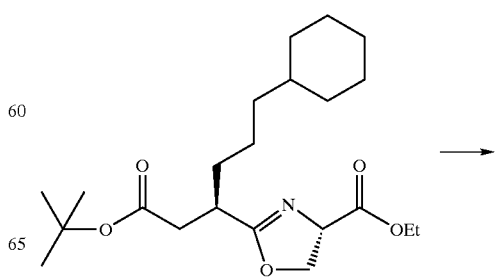

-continued

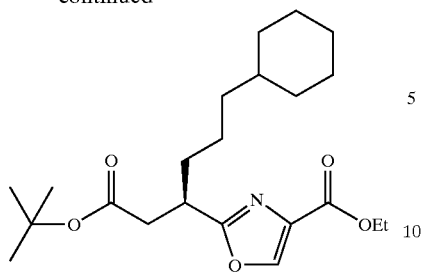

A suspension of copper (II) bromide (2.08 g, 9.31 mmol) and hexamethylenetetramine (1.30 g, 9.31 mmol) In degassed dichloromethane (25 ml) was treated with 1,8-diazabicyclo[5.4.0]undec-7-ene (1.39 ml, 9.31 mmol) and then cooled in a cold water bath and stirred for 5 minutes. This suspension was then treated dropwise with a solution of ethyl (4S)-2-{(1R)-1-[2-(tert-butoxy)-2-oxoethyl]-4-cyclohexylbutyl}-4,5-dihydro-1,3-oxazole-4-carboxylate (Preparation 31) (0.92 g, 2.33 mmol) in dichloromethane (5 ml) and the resulting mixture was stirred at room temperature under a nitrogen atmosphere for 17 hours. The solvent was removed under reduced pressure and the residue partitioned between ethyl acetate and a solution of 0.88 ammonia: saturated aqueous solution of ammonium chloride (1:1, 100 mls). The layers were separated and the aqueous layer was extracted with ethyl acetate (x2). The organic layers were combined, washed sequentially with hydrochloric acid (2M), saturated aqueous sodium hydrogen carbonate solution and brine, dried over anhydrous magnesium sulphate, filtered and the solvent removed under reduced pressure. The residue was purified by column chromatography on silica gel eluting with ethyl acetate: pentane (10:90) to afford the title compound as a pale yellow oil (0.59 g).

Ms: 394 (mH$^+$)

$^1$H-NMR (CDCl$_3$) δ: 8.13 (1H, s), 4.39 (2H, q, J=7 Hz), 3.39 (1H, m), 2.80 (1H, dd, J=17, 8 Hz), 2.58 (1H, dd, J=17, 6 Hz), 1.84–1.53 (7H, m), 1.49–1.02 (20H, m), 0.84 (2H, m)

What is claimed is:

1. A compound of formula I:

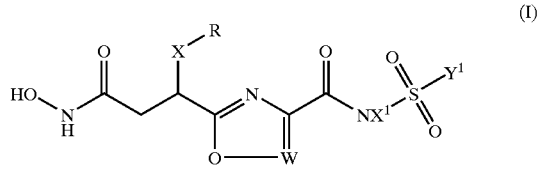

(I)

wherein:
X is C$_{1-6}$ alkylene or C$_{2-4}$ alkenylene, each of which Is optionally substituted by one or more fluorine atoms;
R is aryl, C$_{3-8}$ cycloalkyl or C$_{5-8}$ cycloalkenyl optionally substituted by one or more fluorine atoms,
W is CZ;
Z is H, or C$_1$–C$_4$ alkyl optionally substituted with halogen
X$^1$ is H or C$_1$–C$_4$ alkyl,
Y$^1$ is:
  C$_1$–C$_4$ alkyl, optionally substituted by aryl, or by one or more halogen atoms, with the proviso that when Y$^1$ is methyl, X$^1$ is not H,
  or Y$^1$ is aryl, or a mono or bicyclic non-aromatic carbocyclic or heterocyclic moiety having up to 10 ring atoms and which can have up to 3 ring heteroatoms, independently selected from N, O and S, which ring moiety is optionally substituted by one or more substituents independently selected from halogen, C$_1$–C$_4$ alkoxy and C$_1$–C$_4$ alkyl optionally substituted by one or more halogen,
and the pharmaceutically acceptable salts, solvates, hydrates, and prodrugs thereof.

2. A compound according to claim 1 wherein the stereochemistry is as defined in formula (IA):

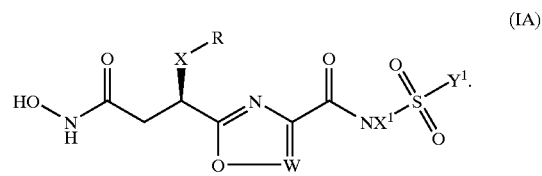

(IA)

3. A compound, salt, solvate or prodrug according to claim 1 wherein X is a linear C$_{2-4}$ alkylene moiety optionally substituted by one or more fluorine atoms.

4. A compound, salt, solvate or prodrug according to claim 3 wherein X is propylene.

5. A compound, salt, solvate or prodrug according to claim 1 wherein R is C$_{3-4}$ cycloalkyl optionally substituted by one or more fluorine atoms.

6. A compound, salt, solvate or prodrug according to claim 5 wherein R Is cyclobutyl or cyclohexyl optionally substituted by one or more fluorine atoms.

7. A compound, salt, solvate or prodrug according to claim 6 wherein R is cyclobutyl or cyclohexyl.

8. A compound, salt, solvate or prodrug according to claim 7 wherein R is cyclohexyl.

9. A compound, salt, solvate or prodrug according to claim 1 wherein W is CH or CCH$_3$.

10. A compound, salt, solvate or prodrug according to claim 1 wherein Y$^1$ is:
  C$_1$–C$_4$ alkyl optionally substituted by phenyl or by one or more halogen atoms;
  phenyl optionally substituted by one or more substituents independently selected from halogen, C$_1$–C$_4$ alkoxy, C$_1$–C$_4$ alkyl optionally substituted with one or more halogen, and which phenyl ring is optionally pyrido-fused;
  a 5- or 6-membered heterocyclic ring with one or two ring heteroatoms selected from N, O and S, which heterocyclic ring is optionally substituted by one or more substituents independently selected from halogen, C$_1$–C$_4$ alkoxy, C$_{1-4}$ alkyl optionally substituted with one or more halogen.

11. A compound, salt, solvate or prodrug according to claim 10 wherein Y$^1$ is phenyl, 4-methylphenyl, 4-methoxyphenyl, 4-fluorophenyl, 4-isopropylphenyl, 3,4-dimethoxyphenyl, 8-quinolinyl, 3,5-dimethyl4-isoxazolyl, isopropyl, methyl, benzyl or 3-pyridyl.

12. A compound, salt, solvate or prodrug according to claim 11 wherein Y$^1$ is phenyl, benzyl, 3,4-dimethoxyphenyl, or 3-pyridyl.

13. A compound, salt, solvate or prodrug according to claim 12 wherein Y$^1$ is phenyl.

14. A compound, salt, solvate or prodrug according to any preceding claim wherein X$^1$ is H or methyl.

15. A compound, salt, solvate or prodrug according to claim 14 wherein X$^1$ is H.

16. A pharmaceutical composition comprising a compound of formula (I), salts thereof, solvates thereof, and/or prodrugs thereof, according to claim 1 and a pharmaceutically acceptable diluent, carrier or adjuvant.

17. A compound according to claim 1 in which X is propylene, R is cyclohexyl, W is CH, Y$^1$ is phenyl and X$^1$ is H.

* * * * *